(12) United States Patent
Torii et al.

(10) Patent No.: US 7,402,643 B2
(45) Date of Patent: Jul. 22, 2008

(54) WATER-ABSORBENT RESIN HAVING TREATED SURFACE AND PROCESS FOR PRODUCING THE SAME

(75) Inventors: Kazushi Torii, Himeji (JP); Taku Iwamura, Himeji (JP); Hiroyuki Ikeuchi, Himeji (JP); Sayaka Machida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 263 days.

(21) Appl. No.: 10/941,873

(22) Filed: Sep. 16, 2004

(65) Prior Publication Data

US 2005/0070671 A1 Mar. 31, 2005

(30) Foreign Application Priority Data

Sep. 19, 2003 (JP) ............................. 2003-328553

(51) Int. Cl.
*C08F 20/06* (2006.01)
*C08F 120/06* (2006.01)

(52) U.S. Cl. .................. 526/317.1; 526/320; 525/329.5
(58) Field of Classification Search .............. 526/317.1, 526/320; 525/329.5
See application file for complete search history.

(56) References Cited

U.S. PATENT DOCUMENTS

| | | | |
|---|---|---|---|
| 3,935,099 A | 1/1976 | Weaver et al. | |
| 3,959,569 A | 5/1976 | Burkholder, Jr. | |
| 4,076,663 A | 2/1978 | Masuda et al. | |
| 4,093,776 A | 6/1978 | Aoki et al. | |
| 4,124,748 A | 11/1978 | Fujimoto et al. | |
| 4,367,323 A | 1/1983 | Kitamura et al. | |
| 4,389,513 A | 6/1983 | Miyazaki | |
| 4,446,261 A | 5/1984 | Yamasaki et al. | |
| 4,625,001 A | 11/1986 | Tsubakimoto et al. | |
| 4,654,039 A | 3/1987 | Brandt et al. | |
| 4,683,274 A | 7/1987 | Nakamura et al. | |
| 4,690,996 A | 9/1987 | Shih et al. | |
| 4,721,647 A | 1/1988 | Nakanishi et al. | |
| 4,738,867 A | 4/1988 | Itoh et al. | |
| 4,748,076 A | 5/1988 | Saotome | |
| 4,769,427 A | 9/1988 | Nowakowsky et al. | |
| 4,771,105 A | 9/1988 | Shirai et al. | |
| 4,873,299 A | 10/1989 | Nowakowsky et al. | |
| 4,950,692 A | 8/1990 | Lewis et al. | |
| 5,115,011 A * | 5/1992 | Harada et al. ................ 524/419 | |
| 5,241,009 A | 8/1993 | Yarbrough et al. | |
| 5,250,640 A | 10/1993 | Irie et al. | |
| 5,264,495 A | 11/1993 | Irie et al. | |
| 5,275,773 A | 1/1994 | Irie et al. | |
| 5,346,485 A | 9/1994 | Yarbrough et al. | |
| 5,478,879 A | 12/1995 | Kajikawa et al. | |
| 5,849,405 A | 12/1998 | Wang et al. | |
| 5,851,672 A | 12/1998 | Wang et al. | |
| 6,099,950 A | 8/2000 | Wang et al. | |
| 6,124,391 A | 9/2000 | Sun et al. | |
| 6,180,724 B1 | 1/2001 | Wada et al. | |
| 6,228,930 B1 | 5/2001 | Dairoku et al. | |
| 6,300,275 B1 | 10/2001 | Weir | |
| 6,433,058 B1 | 8/2002 | Weir et al. | |
| 6,448,320 B1 | 9/2002 | Igarashi et al. | |
| 6,605,673 B1 * | 8/2003 | Mertens et al. .......... 525/329.5 |
| 6,620,889 B1 * | 9/2003 | Mertens et al. ............. 525/221 |
| 2002/0013394 A1 | 1/2002 | Dairoku et al. | |
| 2002/0040095 A1 | 4/2002 | Dairoku et al. | |
| 2002/0128618 A1 | 9/2002 | Frenz et al. | |
| 2002/0165288 A1 | 11/2002 | Frenz et al. | |
| 2002/0169252 A1 | 11/2002 | Wilson | |
| 2002/0193492 A1 | 12/2002 | Wilson | |
| 2003/0092849 A1 | 5/2003 | Dairoku et al. | |
| 2003/0207997 A1 * | 11/2003 | Mertens et al. ............. 525/244 |
| 2004/0071966 A1 * | 4/2004 | Inger et al. .................. 428/394 |

FOREIGN PATENT DOCUMENTS

EP 0 386 897 9/1990

(Continued)

*Primary Examiner*—Ling-Siu Choi
(74) *Attorney, Agent, or Firm*—Roylance, Abrams, Berdo & Goodman, L.L.P.

(57) ABSTRACT

An object of the present invention is to provide: a water-absorbent resin which can sufficiently overcome the problem of the gel blocking, can manifest sufficient absorption capacity without load and sufficient absorption capacity under load and, at the same time, can also exert excellent liquid permeability under load; and a process for producing the same. As a means of achieving this object, a first production process among the processes according to the present invention for producing a water-absorbent resin having a treated surface is a process comprising: a step of mixing a water-absorbent resin having an internal crosslinked structure obtained by polymerizing a monomer containing acrylic acid and/or a salt thereof as a main component, a complex containing a polyvalent metal atom as a central atom and an organic secondary crosslinking agent in the presence of an aqueous liquid; and a step of crosslinking a surface of the water-absorbent resin with the organic secondary crosslinking agent. And a second production process is a process comprising a step of mixing a water-absorbent resin having an internal crosslinked structure and a crosslinked surface obtained by polymerizing a monomer containing acrylic acid and/or a salt thereof as a main component, and a complex containing a polyvalent metal atom as a central atom in the presence of an aqueous liquid.

10 Claims, 2 Drawing Sheets

FOREIGN PATENT DOCUMENTS

| | | |
|---|---|---|
| EP | 0 456 136 | 11/1991 |
| EP | 0 668 080 | 8/1995 |
| EP | 0 702 031 | 3/1996 |
| EP | 0 844 270 | 5/1998 |
| EP | 1 178 059 | 2/2002 |
| JP | 61-46241 | 3/1986 |
| JP | 61-257235 | 11/1986 |
| JP | 62-7745 | 1/1987 |
| JP | 64-56707 | 3/1989 |
| JP | 6-370 | 1/1994 |
| JP | 9-124879 | 5/1997 |
| JP | 9-509591 | 9/1997 |
| JP | 2000-26738 | 1/2000 |
| JP | 2001-96151 | 4/2001 |
| JP | 2001-523289 | 11/2001 |
| JP | 2002-523526 | 7/2002 |
| JP | 2002-539281 | 11/2002 |
| WO | WO 2004/069293 | 8/2004 |
| WO | WO 2004/069915 | 8/2004 |

\* cited by examiner

WATER-ABSORBENT RESIN HAVING TREATED SURFACE AND PROCESS FOR PRODUCING THE SAME

BACKGROUND OF THE INVENTION

A. Technical Field

The present invention relates to a water-absorbent resin having a treated surface and a process for producing the same. More particularly, the present invention relates to: a water-absorbent resin having a treated surface, which has a polyvalent metal atom on a surface of the water-absorbent resin; and a process for producing the same.

B. Background Art

As a sanitary material such as a disposable diaper, a sanitary napkin and an incontinent pad, a water-absorbent structure (also referred to as absorbent structure in some cases) containing a hydrophilic fiber such as a pulp and a water-absorbent resin as constituent materials is widely utilized for the purpose of absorbing a body fluid.

In recent years, high functionalization and thinning of these sanitary materials have progressed, and there is a tendency that the amount of a water-absorbent resin to be used per one sanitary material, and the ratio of the water-absorbent resin relative to the whole water-absorbent structure composed of the water-absorbent resin and the hydrophilic fiber are increased. That is, by reducing the hydrophilic fiber having a small bulk density, and using a large amount of a water-absorbent resin which is excellent in water-absorbing property and has a large bulk density, the ratio of the water-absorbent resin in the water-absorbent structure is enhanced, and the thinning of the sanitary material is tried without reducing the water absorption amount.

However, the sanitary material in which the ratio of the hydrophilic fiber is reduced, and the ratio of the water-absorbent resin is increased like this, is preferable from the viewpoint of simple liquid storage, but when distribution and diffusion of a liquid under circumstances of actual use as a diaper are considered, this is rather problematic. For example, the water-absorbent resin becomes a soft gel by much water absorption (moisture absorption), and there is a problem that gel blocking is caused such that diffusibility of a liquid in a sanitary material (liquid permeability of gel under load) and gel handling property are remarkably reduced. In order to avoid such the problem, and maintain absorption performance of the water-absorbent structure (also referred to as water-absorption performance in some cases), the ratio between the hydrophilic fiber and the water-absorbent resin is naturally limited, and a limitation is also generated in the thinning of the sanitary material.

Then, as means for preventing the aforementioned gel blocking, technique of adding a metal compound (in particular, polyvalent metal compound) to a water-absorbent resin is reported. Specifically, there is the technique of adding a powder of a metal compound (metal salt) such as aluminum sulfate to a water-absorbent resin, and then further adding water (e.g. see patent documents 1 and 2 below). However, since in such the technique, the added metal compound is dissolved and is permeated in the interior, even when the problem of the gel blocking is consequently overcome to thus obtain excellent liquid permeability and liquid diffusibility, a sufficient absorption capacity without load or a sufficient absorption capacity under load cannot be manifested, and there is a problem that desired absorption (water absorption) performance cannot be exerted.

Then, as means for overcoming such the problem, a technique of adding the aforementioned metal salt in the once dissolved state not in the form of the powder to the water-absorbent resin and, thereafter, drying to localize the salt near surfaces of the resin is reported (e.g. see patent document 3 below). In this technique, an attention is paid to a specified polyvalent metal atom, and the metal salt (metal compound) is used.

In addition, the water-absorbent resin exhibits a high absorption capacity when contacting with an aqueous liquid and, due to such water absorption property, the resin also absorbs a moisture in the air (moisture absorption), causing blocking phenomenon in which water-absorbent resin particles are aggregated, and flowability as a powder is lost. Regarding this blocking phenomenon (moisture absorption blocking phenomenon), a problem is known that, during the production of the water-absorbent resin, and during the production of the sanitary material such as a disposable diaper and the like using the water-absorbent resin, blocking and adhesion to apparatus are caused midway of a hopper and a line, so that the handling property is greatly deteriorated, and that the stable production cannot be performed. Thus, as a means for overcoming such the blocking phenomenon (moisture absorption blocking phenomenon), an attempt to add an inorganic compound to a water-absorbent resin is known.

For example, there are the following: a method of mixing an inorganic compound into a water-absorbent resin in which a ratio passing through a sieve of a mesh opening size of 300 μm is about 60% by weight (e.g. see patent document 4 below); a water-insoluble water-absorbent resin composition in which water has been imparted to a mixture of a polyvalent metal salt and a water-absorbent resin (e.g. see patent document 1 below); a production process of scattering water containing a polyvalent metal salt to a water-absorbent resin (e.g. see patent document 5 below); an improved water-absorbent resin in which water containing a polyvalent metal salt has been added to a surface of a water-absorbent resin having a particle size of 5 to 500 μm and this has been heat-treated (e.g. see patent document 6 below), an improved water-absorbent resin obtained by adding water with an inorganic salt dissolved therein to a water-absorbent resin having a crosslinked surface(e.g. see patent document 7 below), and a water-absorbing agent in which a polyvalent metal compound has been added to a water-absorbent resin, and a polyvalent metal is localized near a surface of the water-absorbing agent after water absorption (e.g. see patent document 3 below).

[Patent Document 1] JP-A-257235/1986 (Kokai)
[Patent Document 2] JP-A-523289/2001 (Kohyo)
[Patent Document 3] JP-A-096151/2001 (Kokai)
[Patent Document 4] JP-A-523526/2002 (Kohyo)
[Patent Document 5] JP-A-007745/1987 (Kokai)
[Patent Document 6] JP-A-046241/1986 (Kokai)
[Patent Document 7] JP-A-124879/1997 (Kokai)

However, by such the technique, the problem of the gel blocking and the problem regarding the absorption capacity without load and the absorption capacity under load are overcome to a certain extent, but the liquid permeability under load cannot be said to be on a sufficient level, thus being problematic.

SUMMARY OF THE INVENTION

A. Object of the Invention

Accordingly, an object of the present invention to be achieved is to provide: a water-absorbent resin which can sufficiently overcome the problem of the gel blocking, can manifest sufficient absorption capacity without load and sufficient absorption capacity under load and, at the same time, can also exert excellent liquid permeability under load, and is also excellent in the handling property during the moisture absorption due to exhibition of very-low-level moisture absorption blocking property; and a process for producing the same.

B. Disclosure of the Invention

In order to attain the aforementioned object, the present inventors diligently studied. During its process, first, the present inventors thought that, when localizing a metal on a surface of a water-absorbent resin, there should be selected and used a metal which is not easily permeated into the interior of the aforementioned water-absorbent resin, but has such a size that an interval with an adjacent resin can be retained adequately, and further is little permeated into the interior of a resin during the addition, and can be efficiently present on a resin surface. Thus, the present inventors paid their attention to a complex having a polyvalent metal atom as a central atom among various metal compounds, and considered treating a surface of a water-absorbent resin with this. The present inventors presumed that such the complex of a polyvalent metal atom would have the aforementioned adequate size, and could be efficiently present on a resin surface, as it is (in a state of the polyvalent metal atom and a ligand) or in its modified state (e.g. a product from a reaction with the resin). In addition to the use of the aforementioned complex, the present inventors thought that it is important that a surface of a water-absorbent resin itself is crosslinked. And, actually, the present inventors crosslink-treated a surface of a water-absorbent resin and, at the same time, once dissolved a complex of the aforementioned polyvalent metal atom, and then added it to a water-absorbent resin to mix them together to perform the surface treatment. As a result, the present inventors have found that: surprisingly, the problem of the gel blocking can be sufficiently overcome, and sufficient absorption property is exhibited regarding both of the absorption capacity without load and the absorption capacity under load and, at the same time, a water-absorbent resin which can manifest excellent liquid permeability under load is obtained. And the present inventors have confirmed that the aforementioned problems can be overcome all at once. In this way, the present invention has been completed.

Therefore, of the processes according to the present invention for producing a water-absorbent resin having a treated surface, a first production process is a process comprising: a step of mixing a water-absorbent resin having an internal crosslinked structure obtained by polymerizing a monomer containing acrylic acid and/or a salt thereof as a main component, a complex containing a polyvalent metal atom as a central atom and an organic secondary crosslinking agent in the presence of an aqueous liquid; and a step of crosslinking a surface of the water-absorbent resin with the organic secondary crosslinking agent.

And a second production process is a process comprising a step of mixing a water-absorbent resin having an internal crosslinked structure and a crosslinked surface obtained by polymerizing a monomer containing acrylic acid and/or a salt thereof as a main component, and a complex containing a polyvalent metal atom as a central atom in the presence of an aqueous liquid.

A water-absorbent resin having a treated surface according to the present invention is such that a polyvalent metal atom and a ligand which can coordinate at the polyvalent metal atom and is other than water are present on a surface of a water-absorbent resin having an internal crosslinked structure and a crosslinked surface obtained by polymerizing a monomer containing acrylic acid and/or a salt thereof as a main component.

Another water-absorbent resin having a treated surface according to the present invention is such that a polyvalent metal atom is present on a surface of a water-absorbent resin having an internal crosslinked structure and a crosslinked surface obtained by polymerizing a monomer containing acrylic acid and/or a salt thereof as a main component, wherein the extraction ratio of the polyvalent metal atom is 80% by mass or smaller.

Incidentally, although the technique of treating a water-absorbent resin with a polyvalent metal cation (which is in a form of an aqueous solution) to thus form an ionic bond between a polyvalent metal and a carboxyl group near a resin surface has been already reported (e.g. see JP-A-539281/2002 (Kohyo)), yet, in such the technique, since the ionic bond formed between the polyvalent metal atom and the carboxyl group derived from a cation adsorbed into a water-absorbent resin is easily reversibly dissociated, it is thought that the ionic bond is not actually present near a resin surface, but is permeated into the interior of a resin. Therefore, the performance of retaining an interval with an adjacent resin adequately is not sufficiently exerted as in the above water-absorbent resin according to the present invention, but the liquid permeability, liquid diffusibility and handling property become inferior. In addition, since a cation in an aqueous solution form is widely absorbed and easily permeated into the interior of a water-absorbent resin by also influenced by an electrostatic attracting force with a carboxyl group, a crosslinking effect more than necessary is exerted in a whole interior of a water-absorbent resin and, as a result, there is also a problem that the absorption capacity without load is greatly reduced.

C. Effects of the Invention

According to the present invention, there can be provided: a water-absorbent resin which can sufficiently overcome the problem of the gel blocking, can manifest sufficient absorption capacity without load and sufficient absorption capacity under load and, at the same time, can also exert excellent liquid permeability under load, and is also excellent in the handling property during the moisture absorption due to exhibition of very-low-level moisture absorption blocking property; and a process for producing the same.

These and other objects and the advantages of the present invention will be more fully apparent from the following detailed disclosure.

EXPLANATION OF THE SYMBOLS

Figure 1:
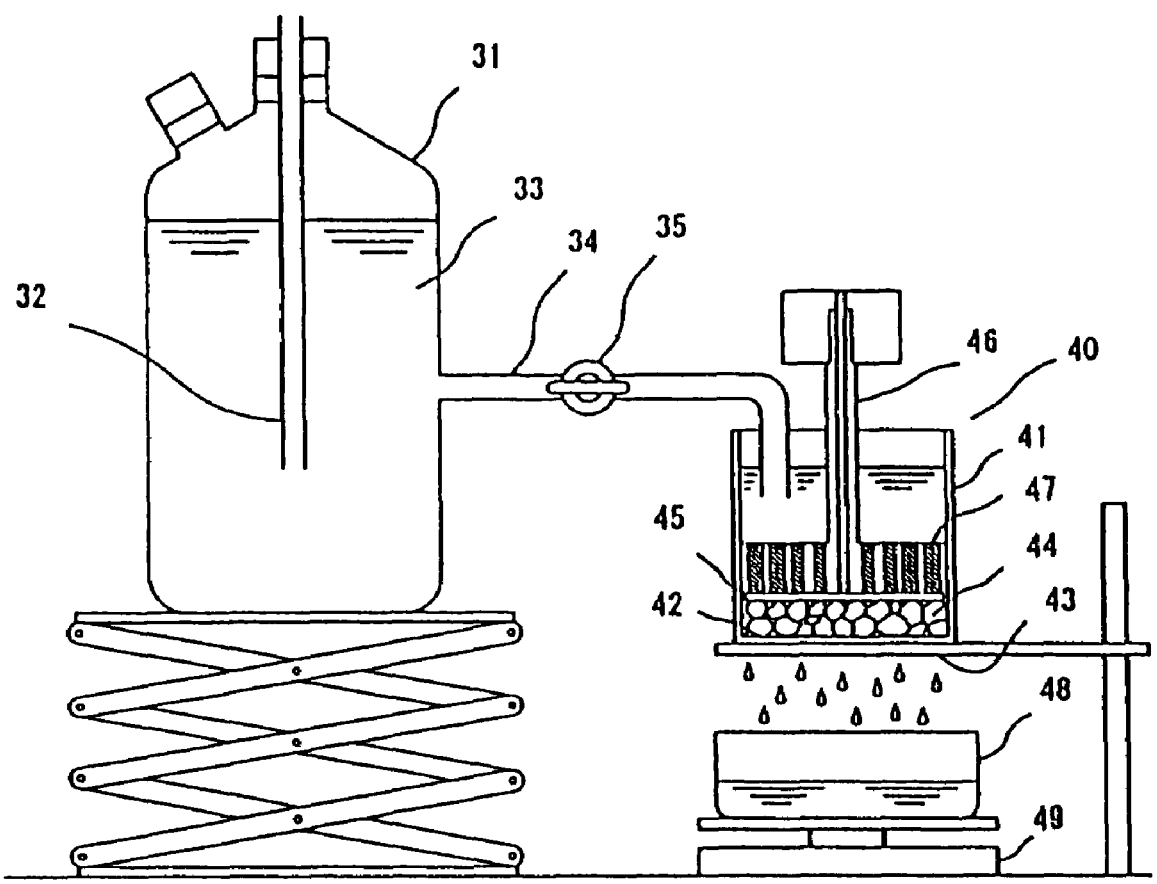
FIG. 1 is a schematic view showing an apparatus for measuring the saline flow conductivity (SFC).

31: Tank
32: Glass tube
33: 0.69 mass % aqueous sodium chloride solution
34: L-tube having cock
35: Cock
40: Receptacle 41: Cell
42: Stainless metal gauze
43: Stainless metal gauze
44: Swollen gel
45: Glass filter
46: Piston
47: Holes in piston
48: Collecting receptacle
49: Balance

DETAILED DESCRIPTION OF THE INVENTION

Hereinafter, detailed descriptions are given about the water-absorbent resin having a treated surface according to the present invention and about the process according to the present invention for producing the water-absorbent resin having a treated surface. However, the scope of the present invention is not bound to these descriptions. And other than the following illustrations can also be carried out in the form of appropriate modifications of the following illustrations within the scope not departing from the spirit of the present invention.

First, the water-absorbent resin (water-absorbent resin used as a raw material) and the complex containing a polyvalent metal atom as a central atom (polyvalent metal complex) in the present invention will be explained. And, subsequently, the process according to the present invention for producing the water-absorbent resin having a treated surface, and the water-absorbent resin having a treated surface according to the present invention, will be explained.

[Water-Absorbent Resin]

The water-absorbent resin in the present invention (water-absorbent resin used as a raw material) is a water-insoluble and water-swellable hydrogel-formable polymer obtainable by polymerizing a hydrophilic monomer, and has an absorption capacity of at least 10 g/g for a physiological saline solution, and preferably has a spherical or irregular particulate shape.

Specific examples of the water-insoluble and water-swellable hydrogel-formable polymer include: partially-neutralized crosslinked poly(acrylic acid) polymers (U.S. Pat. No. 4,625,001, U.S. Pat. No. 4,654,039, U.S. Pat. No. 5,250,640, U.S. Pat. No. 5,275,773, EP 0456136); crosslinked and partially neutralized graft polymers of starch-acrylic acid (U.S. Pat. No. 4,076,663); copolymers of isobutylene-maleic acid (U.S. Pat. No. 4,389,513); saponified copolymers of vinyl acetate-acrylic acid (U.S. Pat. No. 4,124,748); hydrolyzed (co)polymers of acrylamide (U.S. Pat. No. 3,959,569); and hydrolyzed polymers of acrylonitrile (U.S. Pat. No. 3,935,099). The water-absorbent resin in the present invention is a crosslinked poly(acrylic acid) (salt) polymer obtained by polymerizing a monomer containing acrylic acid and/or a salt thereof (at least one kind selected from among acrylic acid and acrylic acid salts) as a main component.

The crosslinked poly(acrylic acid) (salt) polymer is a crosslinked polymer obtained by polymerizing a monomer containing acrylic acid and/or a salt thereof at 50 mole % or more, favorably 70 mole % or more, more favorably 90 mole % or more, of the whole monomer.

Favorably 50 to 90 mole %, more favorably 60 to 80 mole %, of the acid groups in the crosslinked poly(acrylic acid) (salt) polymer is neutralized. Examples of the salt formed by the neutralization include: salts of alkaline metals such as sodium, potassium and lithium; ammonium salts; and amine salts. The neutralization of the water-absorbent resin for forming the salt may be performed in a monomer state before polymerization, or may be performed during polymerization or in a polymer state after polymerization, or both of them may be used.

The water-absorbing rein (crosslinked poly(acrylic acid) (salt) polymer) in the present invention may, if necessary, be a copolymer obtained by copolymerizing another monomer with the monomer which is used as a main component (acrylic acid and/or a salt thereof).

Examples of the above other monomer include: anionic unsaturated monomers (e.g. methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid) and their salts; nonionic-hydrophilic-group-containing unsaturated monomers (e.g. acrylamide, methacrylamide, N-ethyl(meth)acryl amide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine); and cationic unsaturated monomers (e.g. N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, and their quaternary salts). These other monomers may be used either alone respectively or in combinations with each other.

The amount of these other monomers is favorably 0 to 30 mole %, more favorably 0 to 10 mole %, of the whole monomer.

The water-absorbent resin in the present invention is a crosslinked polymer having an internal crosslinked structure.

Examples of a method of introducing an internal crosslinked structure into the water-absorbent resin in the present invention include: a method of introducing by self-crosslinking without using a crosslinking agent; and a method of introducing an internal-crosslinking agent having 2 or more polymerizable unsaturated groups or 2 or more reactive groups by copolymerization or reaction. Preferable is the method of introducing the internal-crosslinking agent by copolymerization or reaction.

Specific examples of the internal-crosslinking agent include N,N'-methylenebis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerin tri(meth)acrylate, glycerin acrylate methacrylate, ethylene-oxide-modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerin, pentaerythritol, ethylenediamine, polyethylenimine, and glycidyl (meth)acrylate. These internal-crosslinking agents may be used either alone respectively or in combinations with each other. From the viewpoint of absorption properties of the resulting water-absorbent resin, it is preferable to essentially use the internal-crosslinking agent having 2 or more polymerizable unsaturated groups.

The amount of the internal-crosslinking agent to be used is favorably 0.005 to 3 mole %, more favorably 0.01 to 1.5 mole %, relative to the whole monomer.

During the polymerization, a hydrophilic polymer (e.g. starch, cellulose, starch derivatives, cellulose derivatives, polyvinyl alcohol, poly(acrylic acid) (salts), and crosslinked poly(acrylic acid) (salts)) or a chain transfer agent (e.g. hypophosphorous acid (salts)) may be added.

When the aforementioned monomer containing acrylic acid and/or a salt thereof as a main component is polymerized in order to obtain the water-absorbent resin in the present invention, it is preferable to aqueous-solution-polymerize the monomer in the form of an aqueous solution from the viewpoint of a performance and easiness of polymerization control, although bulk polymerization, reversed-phase suspension polymerization or precipitation polymerization may be performed. Such the aqueous solution polymerization methods are described, for example, in such as U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690, 996, U.S. Pat. No. 4,721,647, U.S. Pat. No. 4,738,867, U.S. Pat. No. 4,748,076, and EP 1178059.

During the polymerization, such as radical polymerization initiators (e.g. potassium persulfate, ammonium persulfate, sodium persulfate, t-butyl hydroperoxide, hydrogen peroxide, and 2,2'-azobis(2-amidinopropane) dihydrochloride) and active energy rays (e.g. ultraviolet rays and electron beams) can be used. In addition, when the radical polymerization initiator is used, a reducing agent (e.g. sodium sulfite, sodium hydrogensulfite, ferrous sulfate, and L-ascorbic acid) may be used jointly therewith to perform redox polymerization.

The amount of the radical polymerization initiators to be used is favorably 0.001 to 2 mole %, more favorably 0.01 to 0.5 mole %, relative to the whole monomer.

The shape of the water-absorbent resin obtained by the aforementioned polymerization is generally such as an irregular pulverized shape, a spherical shape, a fibrous shape, a bar shape, an approximately spherical shape, or a flat shape. However, the water-absorbent resin in the present invention is desirably a particulate shape. When the resin having such an irregular pulverized shape as obtained by pulverization after drying is used, there are advantages in that the effects of the present invention are more enhanced.

The absorption capacity without load of the water-absorbent resin (having an internal crosslinked structure) in the present invention is favorably 25 to 40 g/g, more favorably 26 to 38 g/g, still more favorably 28 to 36 g/g. If the absorption capacity without load is in the above range, then there are obtained effects, for example, such that the water-absorbent resin which is excellent in the liquid permeability under load can be easily obtained by the below-mentioned surface treatment. When the absorption capacity without load is less than 25 g/g, it may be inferior in the absorption performance. When the absorption capacity without load exceeds 40 g/g, the liquid permeability under load may be inferior.

The water-absorbent resin in the present invention may have a crosslinked surface, that is, may have the crosslinked structure further near a surface thereof. Specifically, as is mentioned below, the water-absorbent resin in the present invention may be surface-crosslinked in advance before being mixed with the complex containing a polyvalent metal as a central atom in the presence of an aqueous liquid (specifically, referring to "before placing the water-absorbent resin in the presence of an aqueous liquid").

Examples of the surface-crosslinking agent (organic secondary crosslinking agent) which can be used during the above surface crosslinking (surface crosslinking which is performed in advance.) include: polyhydric alcohol compounds (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol); epoxy compounds (e.g. ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol); polyamine compounds (e.g. ethylenediamine, diethylenetriamine, triethylenetetramine, tetraethylenepentamine, pentaethylenehexamine, and polyethylenimine) and their inorganic or organic salts (e.g. azetidinium salts); polyisocyanate compounds (e.g. 2,4-tolylene diisocyanate, and hexamethylene diisocyanate); polyoxazoline compounds (e.g. 1,2-ethylenebisoxazoline); alkylene carbonate compounds (e.g. 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one); haloepoxy compounds (e.g. epichlorohydrin, epibromohydrin, and α-methylepichlorohydrin) and their polyamine-added products (e.g. Kymene (registered trademark) produced by Hercules); silane coupling agents (e.g. γ-glycidoxypropyltrimethoxysilane and γ-aminopropyltriethoxysilane); and oxetane compounds (e.g. 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, 3-butyl-3-oxetaneethanol, 3-chloromethyl-3-methyloxetane, 3-chloromethyl-3-ethyloxetane, and polyoxetane compounds). The surface-crosslinking agents may be used either alone respectively or in combinations with each other. Among these surface-crosslinking agents, the polyhydric alcohols are preferable in that they are highly safe and enhance the hydrophilicity of a surface of the water-absorbent resin. In addition, the use of the polyhydric alcohols enhances the affinity of water-absorbent resin surfaces to the polyvalent metal complex, so that interactions between the polyhydric alcohol residue and the polyvalent metal complex surface enable more uniform existence of the polyvalent metal complex (more specifically, the polyvalent metal atom and the ligand which can coordinate at the polyvalent metal atom and is other than water) and/or a modified material thereof (such as a reaction product from the water-absorbent resin and the polyvalent metal complex) on surfaces of the water-absorbent resin.

The amount of the surface-crosslinking agent to be used is favorably 0.001 to 5 parts by mass relative to 100 parts by mass of the solid components of the water-absorbent resin.

When the surface-crosslinking agent and the water-absorbent resin are mixed, water may be used. The amount of water to be used is favorably larger than 0.5 part by mass but not larger than 10 parts by mass, more favorably in the range of 1 part by mass to 5 parts by mass, relative to 100 parts by mass of the solid components of the water-absorbent resin.

When the surface-crosslinking agent or an aqueous solution thereof is mixed, a hydrophilic organic solvent or a third substance may be used as a mixing assistant.

Examples of the hydrophilic organic solvent include: lower alcohols (e.g. methyl alcohol, ethyl alcohol, n-propyl alcohol, isopropyl alcohol, n-butyl alcohol, isobutyl alcohol and t-butyl alcohol); ketones (e.g. acetone); ethers (e.g. dioxane, tetrahydrofuran, and methoxy(poly)ethylene glycol); amides (e.g. ε-caprolactam and N,N-dimethylformamide); sulfoxides (e.g. dimethyl sulfoxide); polyhydric alcohols (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol). The hydrophilic organic solvents may be used either alone respectively or in combinations with each other.

The amount of the hydrophilic organic solvent to be used depends on such as the kind, particle sizes, and water content of the water-absorbent resin, but is favorably in the range of 10 parts by mass or smaller, more favorably in the range of 5 parts by mass or smaller, relative to 100 parts by mass of the solid components of the water-absorbent resin.

As the third substance, there can be cited, for example, such as inorganic acids, organic acids, and polyamino acids described in EP 0668080.

These mixing assistants (hydrophilic organic solvents and third substances) may act as the surface-crosslinking agent, but those which do not reduce the water absorption performance of the water-absorbent resin after its surface-crosslinking are preferable. In the case where volatile alcohols having a boiling point lower than 150° C. are used, they are volatilized during the surface-crosslinking treatment, so their residues do not remain.

In order to uniformly mix the water-absorbent resin and the surface-crosslinking agent, there may be made to coexist non-crosslinkable water-soluble inorganic bases (preferably, alkaline metal salts, ammonium salts, alkaline metal hydroxides, and ammonia or its hydroxide) or non-reducible alkaline metal salt pH buffers (preferably, hydrogencarbonates, dihydrogenphosphates, hydrogenphosphate, etc.) when mixing the water-absorbent resin and the surface-crosslinking agent. The amount of these non-crosslinkable water-soluble inorganic bases and non-reducible alkaline metal salt pH buffers to be used depends on such as the kind and particle sizes of the water-absorbent resin, but is favorably in the range of 0.005 to 10 parts by mass, more favorably in the range of 0.05 to 5 parts by mass, relative to 100 parts by mass of the solid components of the water-absorbent resin.

A method of mixing the water-absorbent resin and the surface-crosslinking agent is not limited. However, examples thereof include: a method including the steps of immersing the water-absorbent resin into the hydrophilic organic solvent and then mixing them with the surface-crosslinking agent (which is, if necessary, dissolved in water and/or the hydrophilic organic solvent); and a method including the step of spraying or dropwise adding the surface-crosslinking agent (which is dissolved in water and/or the hydrophilic organic solvent) directly to the water-absorbent resin to mix them together.

After the water-absorbent resin and the surface-crosslinking agent have been mixed, usually, heating treatment is performed to conduct a crosslinking reaction. The heating treatment temperature depends on the surface-crosslinking agent to be used, but is favorably not lower than 40° C. and not higher than 250° C., more favorably not lower than 150° C. and not higher than 250° C., still more favorably not lower than 160° C. and not higher than 220° C. When the heating treatment temperature is lower than 40° C., the absorption property such as absorption capacity under load is not sufficiently improved in some cases. When the heating treatment temperature exceeds 250° C., deterioration of the water-absorbent resin is caused, and performance is deteriorated in some cases, so caution is needed. The heating treatment time is favorably 1 minute to 2 hours, more favorably 5 minutes to 1 hour.

The particle sizes or particle size distribution of the water-absorbent resin in the present invention is not particularly limited. However, when the water-absorbent resin having relatively small particle sizes and a particle size distribution in which the content of small particle size components is high is used, then there are advantages in that the absorption performance such as water absorption rate and capillary absorption capacity is remarkably improved.

The water-absorbent resin in the present invention has a mass-average particle size of favorably 600 μm or smaller, more favorably 500 to 300 μm, for performance improvement. The water-absorbent resin having such particle sizes can be favorably obtained by pulverizing the water-absorbent resin resultant from the aqueous solution polymerization or by subjecting this pulverized water-absorbent resin to sieving to adjust its particle size. Alternatively, there may be used a water-absorbent resin obtained in a way that: a water-absorbent resin fine powder having particle sizes of 300 μm or smaller is agglomerated and then the particle size is adjusted. Alternatively, there may be used a water-absorbent resin obtained in a way that: irregular pulverized particles of primary particles obtained by the pulverization are partly mixed with the agglomerate of the fine powder. In the case where the agglomerate of the water-absorbent resin is partly mixed, there can be obtained the water-absorbent resin having a treated surface according to the present invention which is more excellent in the absorption property such as water absorption rate and capillary absorption capacity. The amount of the agglomerate of the fine powder to be mixed is favorably 5% by mass or larger, more favorably 10% by mass or larger, still more favorably 15% by mass or larger, of the whole water-absorbent resin.

As methods of producing the agglomerate of the fine powder, publicly known techniques for recycling a fine powder can be used. Examples of usable methods include: a method including the steps of mixing warm water and the fine powder of the water-absorbent resin and then drying the resultant mixture (U.S. Pat. No. 6,228,930); a method including the steps of mixing the fine powder of the water-absorbent resin with an aqueous monomer solution and then polymerizing the resultant mixture (U.S. Pat. No. 5,264,495); a method including the steps of adding water to the fine powder of the water-absorbent resin and then agglomerating them under a specified face pressure or higher (EP 0844270); a method including the steps of sufficiently wetting the fine powder of the water-absorbent resin to form an amorphous gel and then drying and pulverizing this gel (U.S. Pat. No. 4,950,692); and a method including the step of mixing the fine powder of the water-absorbent resin and a polymer gel (U.S. Pat. No. 5,478,879). However, there is preferably used the method including the steps of mixing warm water and the fine powder of the water-absorbent resin and then drying the resultant mixture.

Incidentally, the particle size is indicated by the sieve mesh diameter (sieve mesh opening size) used for the classification.

[Polyvalent Metal Complex]

As to the complex containing a polyvalent metal atom as a central atom (polyvalent metal complex) referred to in the present invention, its definition refers to a complex containing one or more polyvalent metal atoms as central atoms, to which there is bonded another atom or group, that is, a ligand (as such there is a negative, neutral, or positive one), thus forming one group. Its kind or structure is not particularly limited. However, favorable is a complex containing a polyvalent metal atom as a central atom, which is coordinated with one or more ligands other than water. The aforementioned ligand other than water is more favorably a ligand which can form a stronger coordination bond with the aforementioned polyvalent metal atom than water. It is thought that such a complex in which the polyvalent metal atom is coordinated with one or more ligands other than water by a stronger coordination bond than that with water can be present more efficiently on a surface of a water-absorbent resin.

The polyvalent metal atom to be a central atom is not particularly limited. However, favorable examples thereof include at least one kind of metal atom selected from the group consisting of Be, Mg, Ca, Sr, Al, Fe, Mn, Ti and Zr and other transition metals. Trivalent or tetravalent polyvalent metal atoms are favorable. Above all, from the viewpoint of easy formation of a covalent bond with a carboxyl group, at least one kind of metal atom selected from the group consisting of titanium (Ti), zirconium (Zr) and hafnium (Hf) is more favorable, and zirconium (Zr) is particularly favorable.

The ligand which coordinately bonds to the polyvalent metal atom as a central atom is not particularly limited, However, favorable examples thereof include at least one kind selected from the group consisting of a ligand having an OH group, a ligand having a $CO_3$ group, a ligand having an $SO_3$ group, an organic acid (e.g. acetic acid, propionic acid), a chelate-coordinated compound (e.g. phosphoric acid, acetylacetone), and a halogen.

As the ligand which coordinately bonds to the polyvalent metal atom as a central atom, there may be possessed one or more ligands which can be the below-mentioned organic secondary crosslinking agent. However, in this case, it is favorable that there is also possessed one or more ligands other than the ligand which can be the organic secondary crosslinking agent. Examples of such a ligand include a polyhydric alcohol compound, a polyamine compound, an alkylene carbonate compound, 2-oxazolidone and a derivative thereof.

When the complex having the ligand which can be the organic secondary crosslinking agent is used, the organic secondary crosslinking agent remains in the water-absorbent resin at favorably 500 ppm or larger, more favorably 1000 ppm or more.

The polyvalent metal complex referred to in the present invention is, favorably, water-soluble if the complex is water-soluble, then, when mixed with the water-absorbent resin in the presence of an aqueous liquid, the polyvalent metal complex can be made more uniformly present on a surface of the water-absorbent resin.

The polyvalent metal complex referred to in the present invention may be either ionic or nonionic. In addition, when the complex is ionic, it may be either a salt of a complex ion having positive charge (cation complex) or a salt of a complex ion having negative charge (anion complex), thus not particularly limited. If the complex is the nonionic complex and/or the salt of the complex ion having negative charge, then there are advantages in that the complex is little absorbed into the interior of the water-absorbent resin and is therefore still more easily localized on a surface of the water-absorbent resin. Its reason can be considered as follows: Since the carboxyl group derived from acrylic acid and/or a salt thereof used as a main component of the monomer is present throughout the whole water-absorbent resin, it follows that an electrostatic attracting force exerts between this carboxyl group and the salt of the complex ion having positive charge (cation complex), so this salt is absorbed into the interior of the water-absorbent resin more easily than the nonionic complex or the salt of the complex ion having negative charge.

Favorable examples of the above nonionic complex include zirconium acetylacetonate complex, zirconium acetate, and zirconium propionate. These may be used either alone respectively or in combinations with each other.

Favorable examples of the above salt of the complex ion having negative charge include zirconium sulfate, potassium zirconium hexafluoride, sodium zirconium hexafluoride, ammonium zirconium carbonate, potassium zirconium carbonate and sodium zirconium carbonate. Above all, ammonium zirconium carbonate, potassium zirconium carbonate and sodium zirconium carbonate are more favorable because the complex can be sufficiently fixed on a surface of the resin by a chemical bonding reaction accompanied with decarboxylation between the aforementioned carboxyl group possessed by the water-absorbent resin and a carbonate group in the above complex ion having negative charge, and besides, because the effect of crosslinking the resin surface can be also exerted. These may be used either alone respectively or in combinations with each other.

[Process for Producing Water-Absorbent Resin Having Treated Surface]

<First Production Process>

Of the production processes according to the present invention, the first production process is a process for producing a water-absorbent resin having a treated surface, which comprises: a step of mixing a water-absorbent resin having an internal crosslinked structure obtained by polymerizing a monomer containing acrylic acid and/or a salt thereof as a main component, a complex containing a polyvalent metal atom as a central atom (polyvalent metal complex) and an organic secondary crosslinking agent in the presence of an aqueous liquid; and a step of crosslinking a surface of the water-absorbent resin with the organic secondary crosslinking agent.

Details of the water-absorbent resin having an internal crosslinked structure obtained by polymerizing a monomer containing acrylic acid and/or a salt thereof as a main component, and details of the complex containing a polyvalent metal atom as a central atom (polyvalent metal complex), are as described above. However, the above water-absorbent resin is favorably a water-absorbent resin of which the surface has not been crosslinked in advance.

In the first production process, points important for obtaining the water-absorbent resin having a surface on which the polyvalent metal atom is present are as follows: (i) a point that the aforementioned polyvalent metal atom which has been converted into a form of a complex in advance is mixed with the water-absorbent resin; and (ii) a point that a surface of the aforementioned water-absorbent resin has been crosslinked with the organic secondary crosslinking agent. Thereby, the aforementioned object of the present invention can be easily achieved.

In the first production process, the ratio of the polyvalent metal complex to be mixed is favorably 0.01 to 10% by mass, more favorably 0.1 to 5.0% by mass, still more favorably 0.2 to 2.0% by mass, relative to the solid components of the aforementioned water-absorbent resin. When the ratio of the polyvalent metal complex to be mixed is smaller than 0.01% by mass relative to the solid components of the aforementioned water-absorbent resin, there is a possibility that the effect of addition of the polyvalent metal complex is not obtained. When the ratio exceeds 10% by mass, there is a possibility that the absorption capacity without load and the absorption capacity under load are much deteriorated.

In the first production process, by mixing the polyvalent metal complex with the water-absorbent resin in the presence of an aqueous liquid, surface treatment of the water-absorbent resin with the polyvalent metal complex gets performed.

As the organic secondary crosslinking agent which can be used in the first production process, for example, the same as the aforementioned crosslinking agents cited as examples of the surface-crosslinking agent are favorable and, above all, the polyhydric alcohol compounds are more favorable.

The ratio of the organic secondary crosslinking agent to be mixed is favorably 0.01 to 10% by mass, more favorably 0.1 to 5.0% by mass, still more favorably 0.2 to 3.0% by mass, relative to the solid components of the aforementioned water-absorbent resin. When the ratio of the organic secondary crosslinking agent to be mixed is smaller than 0.01% by mass relative to the solid components of the aforementioned water-absorbent resin, there is a possibility that the liquid permeability under load may be reduced. When the ratio exceeds 10% by mass, there is a possibility that the handling property during the water-absorption may be deteriorated due to the remaining organic secondary crosslinking agent.

In order to more accelerate a surface crosslinking reaction with the organic secondary crosslinking agent and more improve the absorption property, inorganic acids, organic acids, polyamino acids or the like described in EP 0668080 may be used jointly with the organic secondary crosslinking agent. The amount of these to be used is different depending on such as pH of the water-absorbent resin, but is favorably 10 parts by mass or smaller, more favorably 0.1 to 5 parts by mass, relative to 100 parts by mass of the water-absorbent resin.

The aqueous liquid which can be used in the first production process is not limited, but publicly known various aqueous media such as water can be used.

The mixing in the presence of the aqueous liquid in the first production process is favorably performed substantially in the absence of an organic solvent. That is, it is favorable that the organic solvent such as alcohols, ethers, esters, aldehydes, ketones, aliphatic hydrocarbons, and aromatic hydrocarbons does substantially not mingle in the above aqueous liquid, and the organic solvent is more favorably smaller than 10% by mass, still more favorably smaller than 1% by mass, relative to the aqueous liquid. When these organic solvents are contained, the polyvalent metal complex becomes easy to deposit, and therefore it becomes difficult to make this complex exist uniformly on a surface of the water-absorbent resin and, finally, there is a possibility that it becomes difficult to obtain a water-absorbent resin which is excellent in the balance among the absorption capacity without load, the absorption capacity under load, and the saline flow conductivity.

The ratio of the aqueous liquid to be blended is not limited. However, it is favorably 0.01 to 10% by mass, more favorably 0.1 to 5% by mass, still more favorably 0.2 to 3% by mass, relative to the solid components of the water-absorbent resin. When the ratio of the aqueous liquid to be blended is smaller than 0.01% by mass relative to the solid components of the water-absorbent resin, the mixability is deteriorated, and there is a possibility that the physical property of the finally obtained water-absorbent resin is reduced. When the ratio exceeds 10% by mass, there is a possibility that the polyvalent metal complex or the organic secondary crosslinking agent is permeated into the interior of the water-absorbent resin too much, and the physical property of the finally obtained water-absorbent resin is reduced.

In the first production process, in order to more uniformly mix the water-absorbent resin, the organic secondary crosslinking agent, and the polyvalent metal complex, there may be made to coexist non-crosslinkable water-soluble inorganic bases (preferably, such as alkaline metal salts, ammonium salts, alkaline metal hydroxides, and ammonia or its hydroxide) or non-reducible alkaline metal salt pH buffers (preferably, hydrogencarbonates, dihydrogenphosphates, hydrogenphosphate, etc.) with the above mixed system. The amount of these to be used can be appropriately set in the favorable range according to such as the kind and size (particle sizes) of the water-absorbent resin, but is, for example, favorably 0.005 to 10 parts by mass, more favorably 0.05 to 5 parts by mass, relative to 100 parts by mass of the solid components of the water-absorbent resin.

In the first production process, the method for mixing such as the water-absorbent resin having an internal crosslinked structure, the polyvalent metal complex, and the organic secondary crosslinking agent may be a method which can uniformly add such as the organic secondary crosslinking agent and the polyvalent metal complex to the water-absorbent resin and mix them, thus not limited. Favorable examples thereof include a method using a mixing apparatus such as cylinder type mixers, V-character-shaped mixers, ribbon type mixers, screw type mixers, twin-arm mixers, pulverizing type kneaders, and Lodge Mixer. Regarding charging into these mixing apparatuses, such as the water-absorbent resin, the organic secondary crosslinking agent and the polyvalent metal complex and the aqueous liquid may be added all at once, or may be added in a dividing manner, or may be added continuously, thus not limited. In addition, the order of adding them is not also limited. Specifically, for example, it may be as follows: the water-absorbent resin having an internal crosslinked structure and the polyvalent metal complex are mixed in the presence of an aqueous liquid in advance and, thereafter, in the presence of this aqueous liquid, separately, the organic secondary crosslinking agent is also added to mix them. Or otherwise, it may be as follows: the water-absorbent resin having an internal crosslinked structure and the organic secondary crosslinking agent are mixed in the presence of the aqueous liquid in advance and, thereafter, in the presence of this aqueous liquid, separately, the polyvalent metal complex is also added to mix them.

In the first production process, the time of mixing the water-absorbent resin having an internal crosslinked structure, the polyvalent metal complex, and the organic secondary crosslinking agent is favorably 10 to 55 minutes, more favorably 15 to 50 minutes, in total. When the mixing time is shorter than 10 minutes, there is a possibility that the water-absorbent resin having the desired performance which can achieve the aforementioned object of the present invention cannot be obtained. When the mixing time exceeds 55 minutes, there is a possibility that the water-absorbent resin is physically (mechanically) damaged, so the desired performance is deteriorated.

In the first production process, the step of mixing such as the water-absorbent resin having an internal crosslinked structure, the polyvalent metal complex, and the organic secondary crosslinking agent is performed in the above way, and further, simultaneously with or after this mixing, a surface of this water-absorbent resin is got crosslinked with the organic secondary crosslinking agent. By doing so, as a result, the crosslinking of the surface of the water-absorbent resin can be also performed in the process of making the polyvalent metal complex exist on the surface of the water-absorbent resin, so the same effect as that of the case where a water-absorbent resin having a pre-crosslinked surface is used (second production process described below) can be obtained. In addition, in the first production process, in particular, since the surface crosslinking with the organic secondary crosslinking agent is performed in a state where the polyvalent metal complex is mixed with the water-absorbent resin, it becomes easy to make the polyvalent metal complex exist uniformly and stably near the surface of the water-absorbent resin, thus there being advantages. Incidentally, it is herein provided that the aforementioned "after this mixing" shall be in the range with a view to circumstances such that the water-absorbent resin is in the presence of the aqueous liquid.

The method of making the aforementioned surface crosslinking performed is not limited. However, for example, there is preferred a method which involves heating the mixed system of such as the water-absorbent resin having an internal crosslinked structure, the polyvalent metal complex, and the organic secondary crosslinking agent. When the surface crosslinking is performed by this heating, it is preferable to heat the above mixed system under stirring. The heating temperature may be set in the favorable range appropriately for the kind of the organic secondary crosslinking agent to be used. For example, when such as the polyhydric alcohol, the polyoxazoline compound or the alkylene carbonate is used as the organic secondary crosslinking agent, 130 to 250° C. is favorable, and 160 to 220° C. is more favorable. When the heating temperature is lower than 130° C., there is a possibility that the surface crosslinking cannot be sufficiently performed to the water-absorbent resin. When the heating temperature exceeds 250° C., there is a possibility that the water-absorbent resin is thermally damaged, so the desired performance is deteriorated. As the heating method, publicly known techniques may be adopted, thus not limited. Favorable examples thereof include a method using a stirring type or fluidized-bed type dryer. Examples of the above dryer include channel type mixing dryers, rotary dryers, disk dryers, fluidized-bed dryers, and air blow type dryers.

When the surface crosslinking is performed by heating, it is favorable to cool the water-absorbent resin after the heating. The cooling temperature is favorably 100 to 20° C., more favorably 80 to 30° C. As the cooling method, publicly known techniques may be adopted, thus not limited. Favorable examples thereof include a method using an apparatus in which a heat medium of the drier used for the above heating is replaced with a cooling medium.

The first production process can further comprise a particle-adjusting step of adjusting the particle size distribution of the water-absorbent resin (obtained via the aforementioned mixing step and the step of performing the surface crosslinking) in a desired range.

<Second Production Process>

Of the production processes according to the present invention, the second production process is a process comprising a step of mixing a water-absorbent resin having an internal crosslinked structure and a crosslinked surface obtained by polymerizing a monomer containing acrylic acid and/or a salt thereof as a main component, and a complex containing a polyvalent metal atom as a central atom (polyvalent metal complex) in the presence of an aqueous liquid.

Details of the above water-absorbent resin (water-absorbent resin used as a raw material) and polyvalent metal complex are as described above. However, in the second production process, there is used, as the above raw water-absorbent resin, a water-absorbent resin having a surface which has been crosslinked in advance before the mixing with the above polyvalent metal complex. Specifically, it can be exemplified by such as: a mode in which there is used a water-absorbent resin having a surface which has been already crosslinked at a point of time when placed in the presence of the above aqueous liquid; and a mode in which the water-absorbent resin having been placed in the presence of the above aqueous liquid is surface-crosslinked before being mixed with the polyvalent metal complex. However, there is no limitation thereto.

In the second production process, a point important for obtaining the water-absorbent resin having a surface on which the polyvalent metal atom is present is that the polyvalent metal atom which has been converted into a form of a complex in advance is mixed with a water-absorbent resin having a pre-crosslinked surface. Thereby, the aforementioned object of the present invention can be easily achieved.

In the second production process, the ratio of the polyvalent metal complex to be mixed is favorably 0.01 to 10% by mass, more favorably 0.1 to 5.0% by mass, still more favorably 0.2 to 2.0% by mass, relative to the solid components of the aforementioned water-absorbent resin. When the ratio of the polyvalent metal complex to be mixed is smaller than 0.01% by mass relative to the solid components of the aforementioned water-absorbent resin, there is a possibility that the effect of addition of the polyvalent metal complex is not obtained. When the ratio exceeds 10% by mass, there is a possibility that the absorption capacity without load and the absorption capacity under load are much deteriorated.

In the second production process, by mixing the polyvalent metal complex with the water-absorbent resin in the presence of an aqueous liquid, surface treatment of the water-absorbent resin with the polyvalent metal complex gets performed.

The aqueous liquid which can be used in the second production process is not limited, but publicly known various aqueous media such as water can be used similarly to the first production process.

The mixing in the presence of the above aqueous liquid is favorably performed substantially in the absence of an organic solvent. Specifically, the explanation about the first production process can be similarly applied.

The ratio of the above aqueous liquid to be blended is not limited. However, it is favorably 0.01 to 10% by mass, more favorably 0.1 to 5% by mass, still more favorably 0.2 to 3% by mass, relative to the solid components of the water-absorbent resin. When the ratio of the above aqueous liquid to be blended is smaller than 0.01% by mass relative to the solid components of the water-absorbent resin, the mixability is deteriorated, and there is a possibility that the physical property of the finally obtained water-absorbent resin is reduced. When the ratio exceeds 10% by mass, there is a possibility that the polyvalent metal complex is permeated into the interior of the water-absorbent resin too much, and the physical property of the finally obtained water-absorbent resin is reduced.

In the second production process, in order to more uniformly mix the water-absorbent resin and the polyvalent metal complex, there may be made to coexist the non-crosslinkable water-soluble inorganic bases or non-reducible alkaline metal salt pH buffers with the above mixed system. Specifically, the explanation about the first production process can be similarly applied.

In the second production process, the method for the aforementioned mixing may be a method which can uniformly add such as the polyvalent metal complex to the water-absorbent resin and mix them, thus not limited. Favorable examples thereof include the same method as the mixing method cited as examples for the first production process. Regarding charging into the mixing apparatus, such as the water-absorbent resin and the polyvalent metal complex and the aqueous liquid may be added all at once, or may be added in a dividing manner, or may be added continuously, thus not limited.

In the second production process, the temperature during the aforementioned mixing is not limited. However, it is favorably room temperature to 100° C., more favorably 40 to 80° C.

In the second production process, the time of the aforementioned mixing is favorably 10 to 55 minutes, more favorably 15 to 50 minutes. When the time of the aforementioned mixing is shorter than 10 minutes, there is a possibility that the water-absorbent resin having the desired performance which can achieve the aforementioned object of the present invention cannot be obtained. When the mixing time exceeds 55 minutes, there is a possibility that the water-absorbent resin is physically (mechanically) damaged, so the desired performance is deteriorated.

Similarly to the first production process, the second production process can further comprise a particle-adjusting step of adjusting the particle size distribution of the water-absorbent resin (obtained via the aforementioned mixing step) in a desired range.

[Water-Absorbent Resin having Treated Surface]

A water-absorbent resin having a treated surface according to the present invention is a water-absorbent resin such that a polyvalent metal atom and a ligand which can coordinate at the polyvalent metal atom and is other than water are present on a surface of a water-absorbent resin having an internal crosslinked structure and a crosslinked surface obtained by polymerizing a monomer containing acrylic acid and/or a salt thereof as a main component.

Another water-absorbent resin having a treated surface according to the present invention is a water-absorbent resin such that a polyvalent metal atom is present on a surface of a water-absorbent resin having an internal crosslinked structure and a crosslinked surface obtained by polymerizing a monomer containing acrylic acid and/or a salt thereof as a main component, wherein the extraction ratio of the polyvalent metal atom is 80% by mass or smaller.

Hereupon, details of the above water-absorbent resin (water-absorbent resin used as a raw material) and polyvalent metal complex are as described above.

An important point in the water-absorbent resin having a treated surface according to the present invention is that a component derived from the polyvalent metal complex is present on a surface of a water-absorbent resin of which the surface has been crosslink-treated (favorably with the organic secondary crosslinking agent). It seems that: thereby proper spaces can be retained between swollen water-absorbent resin particles, so that the aforementioned effects such as high liquid permeability under load can be achieved. The component derived from the polyvalent metal complex, specifically, refers to: the polyvalent metal atom and the ligand (which can coordinate at the polyvalent metal atom) other than water; or a modified material of the polyvalent metal complex (such as a reaction product from the water-absorbent resin and the polyvalent metal complex).

In the case where the polyvalent metal atom and the ligand (which can coordinate at the polyvalent metal atom) other than water are present, as the component derived from the polyvalent metal complex, on the water-absorbent resin surface, then it seems that: the ligand acts when the polyvalent metal atom permeates the inside of the water-absorbent resin, so that the bulkiness on the molecular level increases. Therefore, it seems that the polyvalent metal atom little permeates the inside of the water-absorbent resin and therefore can efficiently be present on the surface.

In the case where the modified material of the polyvalent metal complex (such as a reaction product from the water-absorbent resin and the polyvalent metal complex) is present, as the component derived from the polyvalent metal complex, on the water-absorbent resin surface, then the polyvalent metal atom is much restricted as to diffusion into a liquid because of such as reaction with the water-absorbent resin. Therefore, it seems that the polyvalent metal atom little permeates the inside of the water-absorbent resin and therefore can efficiently be present on the surface. In addition, the polyvalent metal atom in such a state is little extracted by extraction operation. The water-absorbent resin of which the surface has been crosslink-treated has a high crosslinking density near the surface, where the network structure of molecular chains is dense. Therefore, the permeation of the component, derived from the polyvalent metal complex, into the inside of the water-absorbent resin seems to further be prevented.

In the water-absorbent resin according to the present invention, the "ligand which can coordinate at the polyvalent metal atom" is the same as the previously explained "ligand which coordinately bonds to the polyvalent metal atom as a central atom".

In the water-absorbent resin according to the present invention, the case of referring to the modified material of the polyvalent metal complex includes all the modified materials derived from the polyvalent metal complex, thus not limited. Examples thereof include a case where, as a result of the reaction of the ligand or polyvalent metal atom in the polyvalent metal complex with a functional group of the water-absorbent resin, the polyvalent metal atom is chemically bonded thereto. Specifically, favorable examples thereof include a case where, when there is a carbonate group ($CO_3$ group) as a ligand, it has made a reaction (accompanied with decarboxylation) with a carboxyl group of the water-absorbent resin to thus bond thereto.

As an index of the presence of the polyvalent metal atom (as the above modified material) on the water-absorbent resin surface, in the water-absorbent resin according to the present invention, the extraction ratio of the polyvalent metal atom measured by the below-mentioned method is favorably 80% by mass or smaller, more favorably 70% by mass or smaller, still more favorably 60% by mass or smaller. In the case where the polyvalent metal complex has reacted with a functional group (particularly, carboxyl group) of the water-absorbent resin to thus form the modified material, the extraction ratio of the polyvalent metal atom seems to decrease for a reason such that the modified material is bonded to the carboxyl group.

Also, as to the water-absorbent resin according to the present invention, its polyvalent metal atom/carbon ratio, as determined from surface polyvalent metal concentration measurement by Ar ion sputtering and ESCA (illustrated by the below-mentioned measurement method), is at the maximum value in a sputtering time of favorably within 203 seconds, more favorably within 100 seconds. The surface polyvalent metal concentration measurement by Ar ion sputtering and ESCA is such that: while the water-absorbent resin surface is extremely gradually shaved off by the Ar ion sputtering (hereinafter abbreviated to sputtering), the polyvalent metal atom concentration in the shaved-off surface is quantified by the ESCA (which is an abbreviation of Electron Spectroscopy for Chemical Analysis and referred to also as XPS: X-Ray Photoelectron Spectroscopy). This clarifies the polyvalent metal atom concentration distribution in the direction of the depth of the water-absorbent resin surface. The water-absorbent resin according to the present invention is favorably such that: the polyvalent metal atom concentration (polyvalent metal atom/carbon ratio) is high at the water-absorbent resin surface and then becomes lower with the advance toward the inside. The water-absorbent resin surface, as referred to in the present invention, favorably means a range of not more than 203 seconds in sputtering time under the below-mentioned conditions.

The process for producing the "water-absorbent resin according to the present invention" is not limited. However, the aforementioned first production process and second production process can be favorably adopted.

The water-absorbent resin according to the present invention is a particulate (spherical or irregular particulate shape) composition (water-absorbent resin composition) which comprises the aforementioned water-absorbent resin (water-absorbent resin used as a raw material) as a main component, wherein the content of the water-absorbent resin (water-absorbent resin used as a raw material) is favorably 80 to 99.99% by mass, more favorably 90 to 99.90% by mass. When the content of the water-absorbent resin (used as a raw material) in the water-absorbent resin according to the present invention is lower than 80% by mass, there is a possibility that the absorption capacity without load or under load is reduced. When the above content exceeds 99.99% by mass, there is a possibility that the liquid permeability under load is inferior.

Also, the water-absorbent resin according to the present invention contains the polyvalent metal complex (the polyvalent metal atom and the ligand (which can coordinate at the polyvalent metal atom) other than water) and/or its modified material (such as a reaction product from the water-absorbent resin and the polyvalent metal complex) in their total amount of favorably 0.01 to 5% by mass, more favorably 0.01 to 2% by mass. When the content of the polyvalent metal complex and/or its modified material is lower than 0.01% by mass, there. is a possibility that the liquid permeability under load is inferior. When the above content exceeds 5% by mass, there is a possibility that the absorption capacity without load or under load is reduced.

Also, the water-absorbent resin according to the present invention contains the polyvalent metal atom and the ligand (which can coordinate at the polyvalent metal atom) other than water in their total amount of favorably 0.008 to 4% by mass, more favorably 0.008 to 1.6% by mass.

Also, the water-absorbent resin according to the present invention contains a polyvalent metal atom (which is not extracted by the below-mentioned extraction operation) in an amount of favorably 0.002 to 1% by mass, more favorably 0.002 to 0.4% by mass.

The water-absorbent resin according to the present invention is particulate, and its mass-average particle size is favorably 100 to 600 μm, more favorably 200 to 500 μm. When the mass-average particle size is smaller than 100 μm, there is a possibility that the liquid permeability under load is inferior, and besides, a problem of a powder dust arises. When the mass-average particle size is larger than 600 μm, there is a possibility that the absorption rate is slowed, and besides, when used for such as disposable diaper, its top sheet is broken. In addition, in the water-absorbent resin according to the present invention, the content of particles having particle sizes of smaller than 300 μm is favorably 10% by mass or larger, more favorably 30% by mass or larger, still more favorably 50% by mass or larger.

As to the water-absorbent resin according to the present invention, its absorption capacity without load (CRC) is favorably 20 (g/g) or larger, more favorably 22 (g/g) or larger, still more favorably 24 (g/g) or larger, yet still more favorably 25 (g/g) or larger, particularly favorably 27 (g/g) or larger. The absorption capacity without load (CRC) is favorably 500 (g/g) or smaller. When the absorption capacity without load (CRC) is smaller than 20 (g/g), the absorption efficiency is deteriorated when used for sanitary materials such as diapers.

As to the water-absorbent resin according to the present invention, its absorption capacity under load (AAP) is favorably 16 (g/g) or larger, more favorably 18 (g/g) or larger, still more favorably 20 (g/g) or larger, yet still more favorably 22 (g/g) or larger, particularly favorably 24 (g/g) or larger, under a load of 0.7 psi (4.83 kPa). The absorption capacity under load (AAP) is favorably 100 (g/g) or smaller. When the absorption capacity under load (AAP) is smaller than 18 (g/g), the absorption efficiency is deteriorated when used for sanitary materials such as diapers.

As to the water-absorbent resin according to the present invention, its saline flow conductivity (SFC) which corresponds to evaluation of the liquid permeability under load is favorably 30 to 2000 ($\times 10^{-7}$ cm$^3$·s/g), more favorably 50 to 2000 ($\times 10^{-7}$ cm$^3$·s/g), still more favorably 80 to 2000 ($\times 10^{-7}$ cm$^3$·s/g), particularly favorably 100 to 2000 ($\times 10^{-7}$ cm$^3$·s/g). The saline flow conductivity (SFC) depends on the content of the water-absorbent resin in sanitary materials. As this content becomes higher, the higher saline flow conductivity (SFC) becomes necessary.

As to the water-absorbent resin according to the present invention, it is desirable that the absorption capacity under load (AAP) of this water-absorbent resin is small in reduction as compared with an absorption capacity under load (AAP) (under the same load) of a water-absorbent resin to which the polyvalent metal salt powder has not yet been added. The water-absorbent resin according to the present invention maintains its absorption capacity under load (AAP) at favorably 0.85 time or larger, more favorably 0.90 time or larger, still more favorably 0.95 time or larger, as compared with the absorption capacity under load (AAP) of the water-absorbent resin to which the polyvalent metal salt powder has not yet been added.

The water-absorbent resin, according to the present invention, can maintain a high saline flow conductivity (SFC), that is, an excellent liquid permeability under load, even when used in sanitary materials for a long time.

As to the water-absorbent resin according to the present invention, the ratio of a saline flow conductivity (SFC) after a swelling time of 120 minutes to a saline flow conductivity (SFC) after a swelling time of 60 minutes, namely, the retention ratio of the saline flow conductivity (retention ratio of SFC), is favorably not less than 40%, more favorably not less than 50%, still more favorably not less than 60%. As to conventional water-absorbent resins (or water-absorbent resin compositions) to which metal particles have been added, if they are measured for a swelling duration of more than 60 minutes in the test for the saline flow conductivity (SFC), then a rapid fall of the liquid permeation rate is seen.

The moisture absorption blocking property of the water-absorbent resin according to the present invention can be indicated by a moisture absorption blocking ratio (BR). A method for measuring it will be described in detail below. Under conditions of 25° C. and a relative humidity of 90% for 1 hour, the moisture absorption blocking ratio (BR) is favorably 40% or lower, more favorably 30% or lower, still more favorably 20% or lower, particularly favorably 10% or lower. When the moisture absorption blocking ratio (BR) exceeds 40%, there can be occur problems such that: the handling property of the water-absorbent resin under a high humidity is so bad that: when, for example, the below-mentioned thin-type water-absorbent structure for sanitary materials is produced, then, in production plants, the resin aggregates in conveyance pipes to thus cause their clogging, or the resin cannot be uniformly mixed with hydrophilic fibers.

Also, the water-absorbent resin according to the present invention, favorably, further has a feature of little generation of dust. As to the water-absorbent resin according to the present invention, the dust generation degree is favorably not more than 0.25 (mg/m$^3$), more favorably not more than 0.23 (mg/m$^3$), still more favorably not more than 0.20 (mg/m$^3$), yet still more favorably not more than 0.17 (mg/m$^3$), particularly favorably not more than 0.15 (mg/m$^3$).

The water-absorbent resin according to the present invention may possess such functions as given or enhanced by causing this water-absorbent resin to, besides the water-absorbent resin (water-absorbent resin used as a raw material) and the polyvalent metal complex (the polyvalent metal atom and the ligand (which can coordinate at the polyvalent metal atom) other than water) and/or its modified material (such as a reaction product from the water-absorbent resin and the polyvalent metal complex), further contain additives such as: water-insoluble finely-particulate inorganic powders (e.g. silicon dioxide, titanium dioxide, aluminum oxide, magnesium oxide, zinc oxide, talc, calcium phosphate, barium phosphate, silicic acid or its salts, clay, diatomite, zeolite, bentonite, kaolin, hydrotalcite, and salts (e.g. activated clay)); deodorants, perfumes, antibacterial agents, cationic polymer compounds (e.g. polyamines), foaming agents, pigments, dyes, manures, oxidizing agents, and reducing agents. The ratio of the additives as used is favorably less than 10 mass %, more favorably less than 5 mass %, still more favorably less than 1 mass %, relative to the total of the water-absorbent resin (water-absorbent resin used as a raw material) and the polyvalent metal complex (which may be the modified material derived therefrom).

The water-absorbent resin according to the present invention is used for sanitary materials (e.g. disposable diapers, sanitary napkins, incontinent pads, and medical pads). In such a case, this water-absorbent resin is used favorably with a constitution including: (a) a liquid-permeable top sheet placed so as to be adjacent to a wearer's body; (b) a liquid-impermeable back sheet placed so as to be adjacent to the wearer's clothes at a distance from the wearer's body; and (c) the water-absorbent structure placed between the top sheet and the back sheet. The water-absorbent structure may be in more than one layer or used along with such as a pulp layer.

In the case where the water-absorbent resin according to the present invention is used for the sanitary materials, then, in particular, the wettability to aqueous liquids is good, and further, a liquid-absorbed gel little causes the gel-blocking, and spaces between gel particles are not clogged up due to close cohesion of the gel, either. Therefore, even in the case where the water-absorbent resin is used in a high concentration in water-absorbent structures such as diapers, it is possible that, at the second time or thereafter, urine or body fluids diff-use into the water-absorbent structures, without losing a place to go on surfaces of the water-absorbent structures, so that the urine or body fluids can effectively be distributed to the inside water-absorbent resin. Furthermore, a mixture of the water-absorbent resin and its agglomerate has spaces of the appropriate size between water-absorbent resin particles and therefore combines a property of sucking a liquid by the capillary force and therefore can diffuse an absorbed liquid into the entire water-absorbent structure also by the capillary suction force.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to them. Hereinafter, for convenience, the unit "liter(s)" may be referred to simply as "L". In addition, the unit "mass %" may be referred to as "wt %".

The measurement and evaluation methods in the Examples and the Comparative Examples are shown below.

<Absorption Capacity without Load (CRC)>:

An amount of 0.20 g of water-absorbent resin was weighed out precisely to a level of 0.0001 g, and then uniformly placed and sealed into a bag (85 mm×60 mm) made of nonwoven fabric (trade name: Heatron Paper, type: GSP-22, produced by Nangoku Pulp Kogyo Co., Ltd.).

A container of 1 L was charged with 1 L of 0.9 wt % aqueous sodium chloride solution (physiological saline solution), in which one evaluation sample per one container was then immersed for 1 hour. Incidentally, because the present invention is an invention made by directing attention to effects of ion transfer, more than one sample per one container must not be immersed.

After 1 hour, the bag was pulled up and then drained of water by centrifugal force of 250 G with a centrifugal separator (produced by Kokusan Co., Ltd., centrifugal separator: model H-122) for 3 minutes, and then the mass W1 (g) of the bag was measured. In addition, the same procedure as the above was carried out without the water-absorbent resin, and the resultant mass W0 (g) was measured. Then, the absorption capacity (g/g) without load was calculated from these W1 and W0 in accordance with the following equation:

$$CRC(g/g)=[(W1(g)-W0(g))/\text{mass }(g)\text{ of water-absorbent resin}]-1$$

<Absorption Capacity Under Load (AAP)>:

A stainless metal gauze, which was a screen of 400 meshes (mesh opening size: 38 μm), was attached by fusion to a bottom of a plastic supporting cylinder having an inner diameter of 60 mm. Then, under conditions of a room temperature (20 to 25° C.) and a humidity of 50 RH %, onto the above metal gauze, there was uniformly spread 0.9 g of water-absorbent resin, and further thereon, there were mounted a piston and a load in sequence, wherein the piston had an outer diameter of only a little smaller than 60 mm and made no gap with the supporting cylinder, but was not hindered from moving up and down, and wherein the piston and the load were adjusted so that a load of 0.7 psi could uniformly be applied to the water-absorbent resin. Then, the mass Wa (g) of the resultant one set of measurement apparatus was measured.

A glass filter plate having a diameter of 90 mm (produced by Sogo Rikagaku Glass Seisakusho Co., Ltd., pore diameter: 100 to 120 μm) was mounted inside a Petri dish having a diameter of 150 mm, and then a 0.9 wt % aqueous sodium chloride solution (physiological saline solution) (20 to 25° C.) was added up to the same level as the top surface of the glass filter plate, on which a filter paper having a diameter of 90 mm (produced by ADVANTEC Toyo Co., Ltd., trade name: (JIS P 3801, No.2), thickness: 0.26 mm, size of captured particles: 5 μm) was then mounted so that its entire surface would be wetted, and further, an excess of liquid was removed.

The one set of measurement apparatus was mounted on the above wet filter paper, thereby getting the liquid absorbed under the load for a predetermined duration. This absorption duration was defined as 1 hour from the start of the measurement. In addition, during the measurement, a 0.9 mass % aqueous sodium chloride solution (physiological saline solution) was replenished little by little so that the liquid surface of the 0.9 mass % aqueous sodium chloride solution (physiological saline solution) might not become lower than the level at the start of the measurement. Specifically, 1 hour later, the one set of measurement apparatus was removed by being lifted to measure its mass Wb (g). This measurement of the mass must be carried out as quickly as possible and so as not to give any vibration. Then, the absorption capacity under load (AAP) (g/g) was calculated from the Wa and Wb in accordance with the following equation:

$AAP(g/g)=[Wb(g)-Wa(g)]$/mass (g) of water-absorbent resin

<Saline Flow Conductivity (SFC)>:

The following test was carried out according to the saline flow conductivity (SFC) test as described in JP-A-509591/1997 (Kohyo).

An apparatus as shown in FIG. 1 was used, and a water-absorbent resin (0.900 g) as uniformly placed in a receptacle 40 was swollen in synthetic urine (1) under a load of 0.3 psi (2.07 kPa) for 60 minutes (which was 120 minutes in the case of measuring the retention ratio of the saline flow conductivity (SFC)), and the gel layer height of the resultant gel 44 was recorded. Next, under the load of 0.3 psi (2.07 kPa), a 0.69 wt % aqueous sodium chloride solution 33 was passed through the swollen gel layer from a tank 31 under a constant hydrostatic pressure. This SFC test was carried out at room temperature (20 to 25° C). The amount of the liquid passing through the gel layer was recorded as a function to time with a computer and a balance at twenty seconds' intervals for 10 minutes. The rate $F_s$ (t) of the flow passing through the swollen gel 44 (mainly between particles thereof) was determined in a unit of g/s by dividing the incremental mass (g) by the incremental time (s). The time when the constant hydrostatic pressure and the stable flow rate are obtained was represented by $t_s$, and only the data as obtained between $t_s$ and 10 minutes were used for the flow rate calculation. The $F_s$ (t=0) value, namely, the initial rate of the flow passing through the gel layer, was calculated from the flow rates as obtained between $t_s$ and 10 minutes. The $F_s$ (t=0) was calculated by extrapolating the results of a least-squares fit of $F_s$ (t) versus time to t=0.

$$SFC = (F_s(t=0) \times L_0)/(\rho \times A \times \Delta P)$$
$$= (F_s(t=0) \times L_0)/139{,}506$$

where:
$F_s$ (t=0): flow rate denoted by g/s;
$L_0$: initial thickness of gel layer denoted by cm;
$\rho$: density of NaCl solution (1.003 g/cm$^3$);
A: area of top of gel layer in cell 41 (28.27 cm$^2$);
$\Delta P$: hydrostatic pressure applied to gel layer (4,920 dyne/cm$^2$); and
the unit of the SFC is: "$\times 10^{-7}$ cm$^3$·s/g".

As to the apparatus as shown in FIG. 1, a glass tube 32 was inserted in the tank 31, and the lower end of the glass tube 32 was placed so that the 0.69 wt % aqueous sodium chloride solution 33 could be maintained at a height of 5 cm from the bottom of the swollen gel 44 in the cell 41. The 0.69 wt % aqueous sodium chloride solution 33 in the tank 31 was supplied to the cell 41 through an L-tube 34 having a cock. A receptacle 48 to collect the passed liquid was placed under the cell 41, and this collecting receptacle 48 was set on a balance 49. The inner diameter of the cell 41 was 6 cm, and a No. 400 stainless metal gauze (mesh opening size: 38 μm) 42 was set at the bottom thereof. Holes 47 sufficient for the liquid to pass through were opened in the lower portion of a piston 46, and its bottom portion was equipped with a well-permeable glass filter 45 so that the water-absorbent resin or its swollen gel would not enter the holes 47. The cell 41 was placed on a stand to put the cell thereon. The face, contacting with the cell, of the stand was set on a stainless metal gauze 43 that did not inhibit the liquid permeation.

The synthetic urine (1) as used was obtained by mixing together the following: 0.25 g of calcium chloride dihydrate; 2.0 g of potassium chloride; 0.50 g of magnesium chloride hexahydrate; 2.0 g of sodium sulfate; 0.85 g of ammonium dihydrogenphosphate; 0.15 g of diammonium hydrogenphosphate; and 994.25 g of pure water.

<Retention Ratio of Saline Flow Conductivity (SFC) (Retention Ratio of SFC)>:

In the aforementioned method for measurement of the saline flow conductivity (SFC), the swelling time under the load of 0.3 psi (2.07 kPa) is changed from 60 minutes to 120 minutes, and thereafter the measurement is carried out in the same way. When the saline flow conductivity (SFC) as measured after the swelling time of 60 minutes is herein referred to as SFC (1 hr) and when the saline flow conductivity (SFC) as measured after the swelling time of 120 minutes is herein referred to as SFC (2 hr), then the retention ratio of the SFC is represented by the following equation:

Retention ratio (%) of $SFC=[SFC(2\text{ hr})/SFC(1\text{ hr})] \times 100$

<Moisture Absorption Blocking Ratio (BR)>:

An amount of 2.0 g of water-absorbent resin was uniformly spread onto a bottom of a polypropylene-made cup of 50 mm in inner diameter of the bottom and 10 mm in height and then quickly placed into a thermohumidistatic incubator (PLATIOOUS LUCIFER PL-2G, produced by Tabai Espec Co., Ltd.) (which had beforehand been adjusted to 25° C. and the relative humidity of 90%) and then left alone for 60 minutes. Thereafter, the water-absorbent resin having absorbed the moisture was transferred onto a JIS standard sieve of 7.5 cm in diameter and 2,000 μm in mesh opening size and then sieved with a shaking classifier (IIDA SIEVE SHAKER, TYPE: ES-65 type, SER. No. 0501) for 5 minutes. Then, mass W4 (g) of water-absorbent resin remaining on the sieve and mass W5 (g) of water-absorbent resin having passed through the sieve were measured. Incidentally, the operation of from taking the water-absorbent resin out of the thermohumidistatic incubator till measuring the masses W4 (g) and W5 (g) was carried out within 10 minutes.

The moisture absorption blocking ratio (BR) (%) was calculated from the following equation:

Moisture absorption blocking ratio $(BR)$ (%)=[mass $W4(g)/(\text{mass } W4(g)+\text{mass } W5(g))] \times 100$ The lower the moisture absorption blocking ratio (BR) is, the more excellent the moisture absorption flowability is.

<Mass-Average Particle Size>:

The water-absorbent resin was classified with JIS standard sieves having mesh opening sizes of such as 850 μm, 710 μm, 600 μm, 500 μm, 425 μm, 300 μm, 212 μm, 150 μm, and 45 μm. Then, the percentages R of the residues on these sieves were plotted on a logarithmic probability paper. Therefrom, a particle size corresponding to R=50 wt % was read as the mass-average particle size (D50).

As to the classification method for measuring the mass-average particle size (D50), 10.0 g of water-absorbent resin was placed onto JIS standard sieves (having mesh opening sizes of 850 μm, 710 μm, 600 μm, 500 μm, 425 μm, 300 μm, 212 μm, 150 μm, and 45 μm) (THE IIDA TESTING SIEVE: diameter=8 cm) under conditions of a room temperature (20 to 25° C.) and a humidity of 50 RH %, and then classified with a shaking classifier (IIDA SIEVE SHAKER, TYPE: ES-65 type, SER. No. 0501) for 5 minutes.

<Polyvalent Metal Atom Extraction Ratio>:

(Extraction Procedure A):

An amount of 1.0 g of water-absorbent resin was weighed out into a polypropylene-made beaker of 260 ml in capacity, and then thereto an extracting liquid (A) (190.0 g of physiological saline solution (0.9 mass % aqueous NaCl solution) and 10.0 g of 2N hydrochloric acid) was added, and then they were stirred at room temperature for 30 minutes. After the stirring, the resultant supernatant was filtered with a chromatodisk (GL Chromatodisk 25A of GL Science). The filtrate was analyzed with a plasma emission spectrometer (ULTIMA, produced by Horiba Seisakusho) to determine the polyvalent metal concentration. Incidentally, the calibration curve was prepared from the extracting liquid (A) containing a known amount of polyvalent metal atom. Based on the determined polyvalent metal concentration, the ratio of the extracted polyvalent metal atom being extracted from the water-absorbent resin is shown by the following equation:

Extracted polyvalent metal atom (mass %)=polyvalent metal concentration (mass %) in solution×200

(Extraction Procedure B):

The same procedure as the extraction procedure (A) was performed except for replacing the extracting liquid (A) with an extracting liquid (B) (200.0 g of physiological saline solution (0.9 mass % aqueous NaCl solution)).

The result of the extraction procedure A and the result of the extraction procedure B were compared, and whichever was larger in the extracted polyvalent metal atom (mass %) was adopted. Then, from the adopted extracted polyvalent metal atom (mass %), the polyvalent metal atom extraction ratio was determined in accordance with the following equation:

Polyvalent metal atom extraction ratio (mass %)=[extracted polyvalent metal atom (mass %)/polyvalent metal atom (mass %) in water-absorbent resin]×100

Incidentally, the polyvalent metal atom (mass %) in the water-absorbent resin is determined by the following equation:

Polyvalent metal atom (mass %) in water-absorbent resin=[amount (g) of polyvalent metal atom in water-absorbent resin/amount (g) of water-absorbent resin]×100

The amount (g) of the polyvalent metal atom in the water-absorbent resin is, for example, measured by publicly known methods such as fluorescent X-rays, atomic absorption photometry, and plasma emission spectrometry.

<Water-Absorbent Resin Surface Polyvalent Metal Concentration Measurement by Ar Ion Sputtering and ESCA>:

This measurement is such that: while the water-absorbent resin surface is extremely gradually shaved off by the Ar ion sputtering (hereinafter abbreviated to sputtering), the polyvalent metal atom concentration in the shaved-off surface is quantified by the ESCA. This clarifies the polyvalent metal atom concentration distribution in the direction of the depth of the water-absorbent resin surface.

As to the device, JPS-9000MX (produced by JEOL) was used to carry out the measurement. Hereinafter, its details are given.

An electrically conductive tape, having been cut into about 1 cm square, was stuck on a sample stand of a rectangular shape of about 6 cm×about 1 cm, and then onto this tape there was spread about 0.2 g of water-absorbent resin. A portion, having not adhered to the tape, of the water-absorbent resin was blown off by nitrogen gas, and the residual water-absorbent resin was fixed on the tape to such a degree that almost no opening was seen with the eye. This sample stand was placed into a preliminary exhaust room to preliminarily exhaust gases for 16 hours.

The sample was moved into a sample room for the ESCA measurement. Then, scanning was repeated 10 times for each of the objective polyvalent metal atom and carbon atom under conditions having been adjusted according to the elements to be detected (for example, Kα-rays of Mg were used as an excited X-rays source to set acceleration voltage=10 kV, emission current=10 mA, pass energy of detector=10 eV, and energy sweep interval=0.1 eV, and the inner shell levels were set in the range of 176 to 197 eV (including a peak assigned to 3d5/2) for Zr and in the range of 280 to 301 eV (including a peak assigned to 1s) for carbon). As a result, photoelectron spectra were obtained. The value of each element was calculated by carrying out quantitative correction calculation of area values (eV*cps) (as obtained from spectra having been subjected to background correction (carried out by Shirley method)) by use of a relative sensitivity factor as provided to an analytical software as appended to the device. From the resultant values, the polyvalent metal atom/carbon ratio in a sputtering time of 0 second was calculated. The polyvalent metal atom/carbon ratio is calculated from the following equation.

Polyvalent metal atom/carbon ratio=(value of objective polyvalent metal atom)/(value of carbon atom)

Next, the sample was moved into the preliminary exhaust room and then subjected to sputtering under conditions of Ar ion acceleration voltage=500 V, Ar ion acceleration current=8.5 mA, and Ar gas pressure=$3\times10^{-2}$ Pa with a hot-cathode electron impact type (Kaufmann type) ion gun (ion beam current=50 mA, ion beam diameter=1.5 mm) for 3 seconds. After the Ar gas had been exhausted, the sample was moved into the sample room for the measurement and then subjected to the ESCA measurement under the same conditions as aforementioned, thus calculating the polyvalent metal atom/carbon ratio in a sputtering time of 3 seconds.

The sample was moved into the preliminary exhaust room again and then subjected to sputtering for 20 seconds under the same conditions as aforementioned. After the Ar gas had been exhausted, the sample was moved into the sample room for the measurement and then subjected to the ESCA measurement under the same conditions as aforementioned, thus calculating the polyvalent metal atom/carbon ratio in a sputtering time of 23 seconds.

Thereafter, in the same way, the sputtering was further carried out for 60 seconds, 120 seconds, and 300 seconds to calculate the polyvalent metal atom/carbon ratios in sputtering times of 83 seconds, 203 seconds, and 503 seconds respectively (the sputtering time can be set at will).

REFERENTIAL EXAMPLE 1

In a reactor as prepared by lidding a jacketed stainless twin-arm kneader of 10 liters in capacity having two sigma-type blades, there was prepared a reaction liquid by dissolving 11.7 g (0.10 mol %) of polyethylene glycol diacrylate into 5,438 g of aqueous solution of sodium acrylate having a neutralization degree of 71.3 mol % (monomer concentration: 39 wt %). Next, dissolved oxygen was removed from this reaction liquid under an atmosphere of nitrogen gas for 30 minutes. Subsequently, 29.34 g of 10 wt % aqueous sodium persulfate solution and 24.45 g of 0.1 wt % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer was taken out after 30 minutes from the start of the polymerization. The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 180° C. for 40 minutes, thus obtaining a water-absorbent resin (A) which was of the irregular shape and easy to pulverize, such as in the form of particles, a powder, or a particulate dried material agglomerate. The resultant water-absorbent resin (A) was pulverized with a roll mill and then further classified with a JIS standard sieve having a mesh opening size of 850 μm. Next, particles having passed through the 850 μm in the aforementioned operation were classified with a JIS standard sieve having a mesh opening size of 150 μm, whereby a water-absorbent resin having passed through the JIS standard sieve having the mesh opening size of 150 μm was removed, thus obtaining a particulate water-absorbent resin (A1). In addition, similarly, the resultant water-absorbent resin (A) was pulverized with a roll mill and then further classified with a JIS standard sieve having a mesh opening size of 710 μm. Next, particles having passed through the 710 μm in the aforementioned operation were classified with a JIS standard sieve having a mesh opening size of 150 μm, whereby water-absorbent resin particles having passed through the JIS standard sieve having the mesh opening size of 150 μm were removed, thus obtaining a particulate water-absorbent resin (A2). In addition, similarly, the resultant water-absorbent resin (A) was pulverized with a roll mill and then further classified with a JIS standard sieve having a mesh opening size of 600 μm. Next, particles having passed through the 600 μm in the aforementioned operation were classified with a JIS standard sieve having a mesh opening size of 150 μm, whereby water-absorbent resin particles having passed through the JIS standard sieve having the mesh opening size of 150 μm were removed, thus obtaining a particulate water-absorbent resin (A3).

EXAMPLE 1

An amount of 100 g of the water-absorbent resin (A1) having been obtained from Referential Example 1 was uniformly mixed with a surface-treating agent comprising a mixed liquid of 1.0 g of ethylene glycol, 3.0 g of pure water, and 1.0 g of Bacote 20 (ammonium zirconium carbonate, an aqueous solution of 20 wt % as zirconium oxide, produced by MELchemicals), and then the resultant mixture was heat-treated at 180° C. for 30 minutes while being stirred in a mortar mixer. Furthermore, the resultant particles were disintegrated to such a degree that they could pass through a JIS standard sieve having a mesh opening size of 850 μm. As a result, a water-absorbent resin (1) was obtained. The results of having measured the physical properties of the water-absorbent resin (1) are shown in Table 1.

COMPARATIVE EXAMPLE 1

An amount of 100 g of the water-absorbent resin (A1) having been obtained from Referential Example 1 was uniformly mixed with a surface-treating agent comprising a mixed liquid of 1.0 g of ethylene glycol, 3.0 g of pure water, and 0.5 g of aluminum sulfate tetradecahydrate, and then the resultant mixture was heat-treated at 180° C. for 30 minutes while being stirred in a mortar mixer. Furthermore, the resultant particles were disintegrated to such a degree that they could pass through a JIS standard sieve having a mesh opening size of 850 μm. As a result, a water-absorbent resin (c1) was obtained. The results of having measured the physical properties of the water-absorbent resin (c1) are shown in Table 1.

COMPARATIVE EXAMPLE 2

An amount of 30 g of the water-absorbent resin (A1) having been obtained from Referential Example 1 was uniformly mixed with 3.6 g of ethylene glycol and then further with 7.2 g of aqueous ammonium zirconium carbonate solution (aqueous solution of 13.1 wt % as zirconium oxide), and then the resultant mixture was heat-treated at 100° C. for 60 minutes. Furthermore, the resultant particles were disintegrated to such a degree that they could pass through a JIS standard sieve having a mesh opening size of 850 μm. As a result, a water-absorbent resin (c2) was obtained. The results of having measured the physical properties of the water-absorbent resin (c2) are shown in Table 1.

COMPARATIVE EXAMPLE 3

An amount of 100 g of the water-absorbent resin (A1) having been obtained from Referential Example 1 was uniformly mixed with a surface-treating agent comprising a mixed liquid of 10 g of ethylene glycol and 30 g of pure water, and then the resultant mixture was heat-treated at 180° C. for 30 minutes while being stirred in a mortar mixer. Furthermore, the resultant particles were disintegrated to such a degree that they could pass through a JIS standard sieve having a mesh opening size of 850 μm. As a result, a water-absorbent resin (c3) was obtained. The results of having measured the physical properties of the water-absorbent resin (c3) are shown in Table 1.

TABLE 1

|  | Water-absorbent resin | Reaction conditions | Aqueous liquid | Polyvalent metal complex | Organic secondary crosslinking agent | Other component | CRC (g/g) | SFC ($\times 10^{-7}$ cm$^3 \cdot$ s/g) | AAP (g/g) |
|---|---|---|---|---|---|---|---|---|---|
| Referential Example 1 | (A) | — | — | — | — | — | 33.4 | — | — |
| Example 1 | (1) | 180° C. 30 minutes | Pure water | Bacote 20 | EG | — | 28.2 | 150 | 23.7 |
| Comparative Example 1 | (c1) | 180° C. 30 minutes | Pure water | — | EG | ASH14W | 28.0 | 98 | 22.5 |

TABLE 1-continued

| | Water-absorbent resin | Reaction conditions | Aqueous liquid | Polyvalent metal complex | Organic secondary crosslinking agent | Other component | CRC (g/g) | SFC ($\times 10^{-7}$ cm$^3 \cdot$ s/g) | AAP (g/g) |
|---|---|---|---|---|---|---|---|---|---|
| Comparative Example 2 | (c2) | 100° C. 60 minutes | Pure water + EG | AZC | — | — | 22.4 | 124 | 18.7 |
| Comparative Example 3 | (c3) | 180° C. 30 minutes | Pure water | — | EG | — | 28.1 | 62 | 24.1 |

(Notes)
EG: Ethylene glycol
ASH14W: Aluminum sulfate tetradecahydrate
AZC: Ammonium zirconium carbonate

EXAMPLE 2

An amount of 100 g of the water-absorbent resin (A2) having been obtained from Referential Example 1 was uniformly mixed with a surface-treating agent comprising a mixed liquid of 0.7 g of ethylene carbonate, 2.2 g of pure water, and 1.0 g of aqueous zirconium acetate solution (aqueous solution of 30 wt % as zirconium oxide), and then the resultant mixture was heat-treated at 180° C. for 30 minutes while being stirred in a mortar mixer. Furthermore, the resultant particles were disintegrated to such a degree that they could pass through a JIS standard sieve having a mesh opening size of 710 µm. As a result, a water-absorbent resin (2) was obtained. The results of having measured the physical properties of the water-absorbent resin (2) are shown in Table 2.

COMPARATIVE EXAMPLE 4

An amount of 100 g of the water-absorbent resin (A2) having been obtained from Referential Example 1 was uniformly mixed with a surface-treating agent comprising a mixed liquid of 0.7 g of ethylene carbonate, 2.2 g of pure water, and 0.8 g of aluminum sulfate octadecahydrate, and then the resultant mixture was heat-treated at 180° C. for 30 minutes while being stirred in a mortar mixer. Furthermore, the resultant particles were disintegrated to such a degree that they could pass through a JIS standard sieve having a mesh opening size of 710 µm. As a result, a water-absorbent resin (c4) was obtained. The results of having measured the physical properties of the water-absorbent resin (c4) are shown in Table 2.

EXAMPLE 3

An amount of 100 g of the water-absorbent resin (A3) having been obtained from Referential Example 1 was uniformly mixed with a surface-treating agent comprising a mixed liquid of 0.3 g of 1,4-butanediol, 0.5 g of propylene glycol, 0.77 g of pure water, and 1.0 g of Bacote 20 (ammonium zirconium carbonate, an aqueous solution of 20 wt % as zirconium oxide, produced by MELchemicals), and then the resultant mixture was heat-treated at 180° C. for 35 minutes while being stirred in a mortar mixer. Furthermore, the resultant particles were disintegrated to such a degree that they could pass through a JIS standard sieve having a mesh opening size of 600 µm. As a result, a water-absorbent resin (3) was obtained. The results of having measured the physical properties of the water-absorbent resin (3) are shown in Table 3.

EXAMPLE 4

An amount of 100 g of the water-absorbent resin (A3) having been obtained from Referential Example 1 was uniformly mixed with a surface-treating agent comprising a mixed liquid of 0.3 g of 1,4-butanediol, 0.5 g of propylene glycol, 2.5 g of pure water, and 1.0 g of Zirmel 1000 (potassium zirconium carbonate, an aqueous solution of 20 wt % as zirconium oxide, produced by MELchemicals), and then the resultant mixture was heat-treated at 180° C. for 35 minutes while being stirred in a mortar mixer. Furthermore, the resultant particles were disintegrated to such a degree that they could pass through a JIS standard sieve having a mesh opening size of 600 µm. As a result, a water-absorbent resin (4) was

TABLE 2

| | Water-absorbent resin | Reaction conditions | Aqueous liquid | Polyvalent metal complex | Organic secondary crosslinking agent | Other component | CRC (g/g) | SFC ($\times 10^{-7}$ cm$^3 \cdot$ s/g) | AAP (g/g) |
|---|---|---|---|---|---|---|---|---|---|
| Example 2 | (2) | 180° C. 30 minutes | Pure water | ZAc | EC | — | 27.1 | 143 | 23.1 |
| Comparative Example 4 | (c4) | 180° C. 30 minutes | Pure water | — | EC | ASH18W | 27.0 | 118 | 21.3 |

(Notes)
EC: Ethylene carbonate
ZAc: Zirconium acetate
ASH18W: Aluminum sulfate octadecahydrate obtained. The results of having measured the physical properties of the water-absorbent resin (4) are shown in Table 3.

COMPARATIVE EXAMPLE 5

An amount of 100 g of the water-absorbent resin (A3) having been obtained from Referential Example 1 was uniformly mixed with a surface-treating agent comprising a mixed liquid of 0.3 g of 1,4-butanediol, 0.5 g of propylene glycol, 2.5 g of pure water, and 0.5 g of aluminum chloride hexahydrate, and then the resultant mixture was heat-treated at 180° C. for 35 minutes while being stirred in a mortar mixer. Furthermore, the resultant particles were disintegrated to such a degree that they could pass through a JIS standard sieve having a mesh opening size of 600 μm. As a result, a water-absorbent resin (c5) was obtained. The results of having measured the physical properties of the water-absorbent resin (c5) are shown in Table 3.

COMPARATIVE EXAMPLE 6

An amount of 100 g of the water-absorbent resin (A3) having been obtained from Referential Example 1 was uniformly mixed with a surface-treating agent comprising a mixed liquid of 0.3 g of 1,4-butanediol, 0.5 g of propylene glycol, and 2.5 g of pure water, and then the resultant mixture was heat-treated at 180° C. for 35 minutes while being stirred in a mortar mixer. Furthermore, the resultant particles were disintegrated to such a degree that they could pass through a JIS standard sieve having a mesh opening size of 600 μm. As a result, a water-absorbent resin (c6) was obtained. The results of having measured the physical properties of the water-absorbent resin (c6) are shown in Table 3.

absorbent resin (5) was obtained. The results of having measured the physical properties of the water-absorbent resin (5) are shown in Table 4.

EXAMPLE 6

An amount of 100 g of the water-absorbent resin (c6) having been obtained from Comparative Example 6 was uniformly mixed with 2.0 g of Bacote 20 (ammonium zirconium carbonate, an aqueous solution of 20 wt % as zirconium oxide, produced by MELchemicals), and then the resultant mixture was dried at 100° C. for 20 minutes. Furthermore, the resultant particles were disintegrated to such a degree that they could pass through a JIS standard sieve having a mesh opening size of 600 μm. As a result, a water-absorbent resin (6) was obtained. The results of having measured the physical properties of the water-absorbent resin (6) are shown in Table 4.

EXAMPLE 7

An amount of 100 g of the water-absorbent resin (c6) having been obtained from Comparative Example 6 was uniformly mixed with 2.0 g of Zirmel 1000 (potassium zirconium carbonate, an aqueous solution of 20 wt % as zirconium oxide, produced by MELchemicals), and then the resultant mixture was dried at 100° C. for 20 minutes. Furthermore, the resultant particles were disintegrated to such a degree that they could pass through a JIS standard sieve having a mesh opening size of 600 μm. As a result, a water-absorbent resin (7) was obtained. The results of having measured the physical properties of the water-absorbent resin (7) are shown in Table 4. Also shown in Table 5 are the sputtering times and the

TABLE 3

| | Water-absorbent resin | Reaction conditions | Aqueous liquid | Polyvalent metal complex | Organic secondary crosslinking agent | Other component | CRC (g/g) | SFC ($\times 10^{-7}$ cm$^3$ · s/g) | AAP (g/g) |
|---|---|---|---|---|---|---|---|---|---|
| Example 3 | (3) | 180° C. 35 minutes | Pure water | Bacote 20 | BD + PG | — | 26.3 | 166 | 22.5 |
| Example 4 | (4) | 180° C. 35 minutes | Pure water | Zirmel 1000 | BD + PG | — | 26.1 | 138 | 24.5 |
| Comparative Example 5 | (c5) | 180° C. 65 minutes | Pure water | — | BD + PG | AlCl$_3$•6W | 26.0 | 97 | 22.5 |
| Comparative Example 6 | (c6) | 180° C. 35 minutes | Pure water | — | BD + PG | — | 26.0 | 51 | 23.3 |

(Notes)
BD: 1,4-Butanediol
PG: Propylene glycol
AlCl$_3$•6W: Aluminum chloride hexahydrate

EXAMPLE 5

An amount of 100 g of the water-absorbent resin (c6) having been obtained from Comparative Example 6 was uniformly mixed with 2.0 g of aqueous zirconium acetate solution (aqueous solution of 30 wt % as zirconium oxide), and then the resultant mixture was dried at 100° C. for 20 minutes. Furthermore, the resultant particles were disintegrated to such a degree that they could pass through a JIS standard sieve having a mesh opening size of 600 μm. As a result, a water-polyvalent metal (Zr) atom/carbon ratios of the water-absorbent resins (7) and (c6) as determined from the water-absorbent resin surface polyvalent metal concentration measurement by the Ar ion sputtering and the ESCA.

Figure 2:
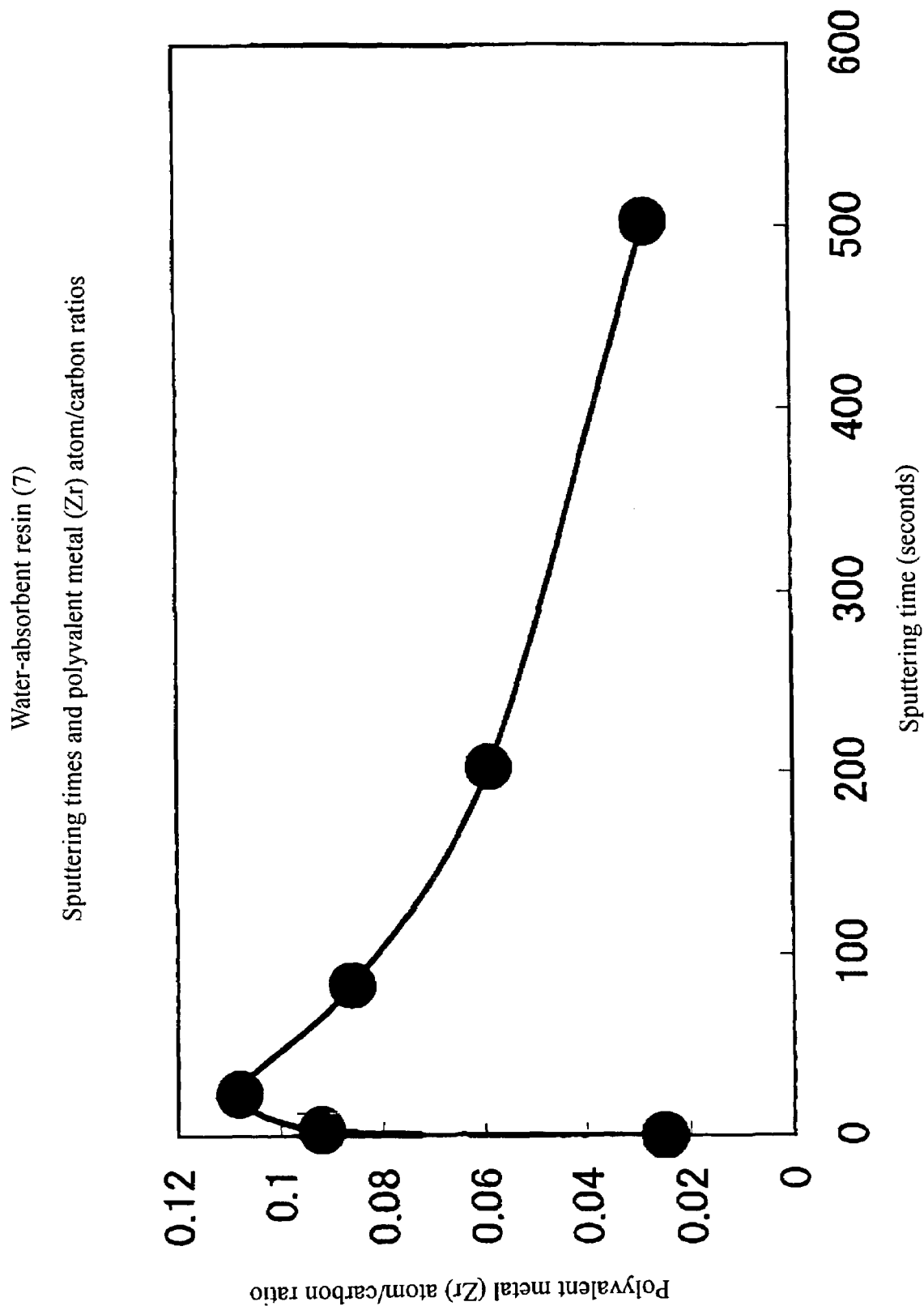
FIG. 2 is a graph showing the sputtering times and the polyvalent metal (Zr) atom/carbon ratios of the water-absorbent resin (7) (obtained from Example 7) as determined from the water-absorbent resin surface polyvalent metal concentration measurement by the Ar ion sputtering and the ESCA.

Shown in FIG. 2 are the sputtering times and the polyvalent metal (Zr) atom/carbon ratios of the water-absorbent resin (7) as determined from the water-absorbent resin surface polyvalent metal concentration measurement by the Ar ion sputtering and the ESCA. The horizontal axis indicates the sputtering time, and the vertical axis indicates the polyvalent metal (Zr) atom/carbon ratio. Therefrom, it can be understood that: as the sputtering time becomes longer (as the depth into the inside of the water-absorbent resin increases), the polyvalent metal (Zr) atom/carbon ratio descreases.

COMPARATIVE EXAMPLE 7

An amount of 100 g of the water-absorbent resin (c6) having been obtained from Comparative Example 6 was uniformly mixed with 2.0 g of aqueous aluminum sulfate octadecahydrate solution (aqueous solution of 20 wt % as aluminum sulfate octadecahydrate), and then the resultant mixture was dried at 100° C. for 20 minutes. Furthermore resultant particles were disintegrated to such a degree that they could pass through a JIS standard sieve having a mesh opening size of 600 μm. As a result, a water-absorbent resin (c7) was obtained. The results of having measured the physical properties of the water-absorbent resin (c7) are shown in Table 4.

TABLE 4

|  | Water-absorbent resin | Aqueous liquid | Polyvalent metal complex | Other component | CRC (g/g) | SFC (×$10^{-7}$ cm³·s/g) | AAP (g/g) |
|---|---|---|---|---|---|---|---|
| Comparative Example 6 | (c6) | — | — | — | 26.0 | 51 | 23.3 |
| Example 5 | (5) | Pure water | ZAc | — | 25.9 | 128 | 22.5 |
| Example 6 | (6) | Pure water | Bacote 20 | — | 25.8 | 130 | 22.4 |
| Example 7 | (7) | Pure water | Zirmel 1000 | — | 25.8 | 131 | 22.1 |
| Comparative Example 7 | (c7) | Pure water | — | ASH18W | 25.6 | 74 | 21.2 |

(Notes)
ZAc: Zirconium acetate
ASH18W: Aluminum sulfate octadecahydrate

TABLE 5

|  | Polyvalent metal (Zr) atom/carbon ratio | |
|---|---|---|
| Sputtering time (seconds) | Water-absorbent resin (7) | Water-absorbent resin (c6) |
| 0 | 0.025 | 0.000 |
| 3 | 0.092 | 0.000 |
| 23 | 0.108 | 0.000 |
| 83 | 0.086 | 0.000 |
| 203 | 0.059 | 0.000 |
| 503 | 0.028 | 0.000 |

[Evaluation of Moisture Absorption Blocking Ratio (BR)]

The water-absorbent resins (A), (1) to (4), and (c1) to (c6), having been obtained from Referential Example 1, Examples 1 to 4, and Comparative Examples 1 to 6, were measured by the moisture absorption blocking ratio (BR). The results are shown in Table 6.

TABLE 6

|  | Water-absorbent resin | Moisture absorption blocking ratio (BR) (%) |
|---|---|---|
| Referential Example 1 | (A) | 100 |
| Example 1 | (1) | 0 |
| Example 2 | (2) | 0 |
| Example 3 | (3) | 0 |
| Example 4 | (4) | 0 |
| Comparative Example 1 | (c1) | 85 |
| Comparative Example 2 | (c2) | 1 |
| Comparative Example 3 | (c3) | 100 |
| Comparative Example 4 | (c4) | 98 |
| Comparative Example 5 | (c5) | 95 |
| Comparative Example 6 | (c6) | 100 |

[Evaluation of Polyvalent Metal Atom Extraction Ratio]

The water-absorbent resins (1) to (6), (c1), (c4), (c5) and (c7), having been obtained from Examples 1 to 6 and Comparative Examples 1, 4, 5 and 7, were measured by the polyvalent metal atom extraction ratio. The results are shown in Table 7.

TABLE 7

|  | Water-absorbent resin | Polyvalent metal atom extraction ratio (%) |
|---|---|---|
| Example 1 | (1) | 3 |
| Example 2 | (2) | 1 |
| Example 3 | (3) | 3 |
| Example 4 | (4) | 3 |
| Example 5 | (5) | 55 |
| Example 6 | (6) | 52 |
| Comparative Example 1 | (c1) | 100 |
| Comparative Example 4 | (c4) | 100 |
| Comparative Example 5 | (c5) | 100 |

TABLE 7-continued

| | Water-absorbent resin | Polyvalent metal atom extraction ratio (%) |
|---|---|---|
| Comparative Example 7 | (c7) | 100 |

INDUSTRIAL APPLICATION

The water-absorbent resin according to the present invention is, for example, favorably used for sanitary materials (e.g. disposable diapers, sanitary napkins, incontinent pads, and medical pads).

The production process according to the present invention can be favorably used for producing the above water-absorbent resin according to the present invention.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbent resin having a treated surface, wherein a trivalent or tetravalent polyvalent metal atom is present on a surface of a water-absorbent resin having an internal crosslinked structure and a crosslinked surface obtained by polymerizing a monomer containing acrylic acid and/or a salt thereof as a main component, wherein the extraction ratio of the polyvalent metal atom is 80% by mass or smaller.

2. The water-absorbent resin having a treated surface according to claim 1, wherein the polyvalent metal atom is at least one kind of metal atom selected from the group consisting of Ti, Zr, and Hf.

3. The water-absorbent resin having a treated surface according to claim 1, wherein the saline flow conductivity (SFC) is 30 to 2000 ($\times 10^{-7}$ cm$^3$·s/g).

4. The water-absorbent resin having a treated surface according to claim 1, wherein the polyvalent metal atom/carbon ratio, as determined from surface polyvalent metal concentration measurement by Ar ion sputtering and ESCA, is at the maximum value in a sputtering time of within 203 seconds.

5. The water-absorbent resin having a treated surface according to claim 1, which has a mass-average particle size of 100 to 600 μm.

6. The water-absorbent resin having a treated surface according to claim 1, which is surface-crosslinked by a surface-crosslinking agent including polyhydric alcohol compounds.

7. The water-absorbent resin having a treated surface according to claim 1, which is obtained by surface-crosslinking of the water-absorbent resin having an amount of an agglomerate of a fine powder of 5% by mass or larger.

8. The water-absorbent resin having a treated surface according to claim 1, wherein the polyvalent metal atom is derived from a water-soluble complex containing a polyvalent metal.

9. The water-absorbent resin having a treated surface according to claim 1, which has an absorption capacity without load (CRC) of 25 g/g or larger and a saline flow conductivity (SFC) of 80 to 2000 ($\times 10^{-7}$ cm$^3$·s/g).

10. The water-absorbent resin having a treated surface according to claim 1, which contains a polyvalent metal atom which is not extracted by the extraction operation in an amount of 0.002 to 1% by mass.

* * * * *